US011129848B2

(12) United States Patent
Perricone

(10) Patent No.: US 11,129,848 B2
(45) **Date of Patent: *Sep. 28, 2021**

(54) MEDICATION ENHANCEMENT USING HYDROGEN

(71) Applicant: Perricone Hydrogen Water Company, LLC, Meriden, CT (US)

(72) Inventor: Nicholas V. Perricone, Madison, CT (US)

(73) Assignee: Perricone Hydrogen Water Company, LLC, Meriden, CT (US)

( * ) Notice: Subject to any disclaimer, the term of this patent is extended or adjusted under 35 U.S.C. 154(b) by 2 days.

This patent is subject to a terminal disclaimer.

(21) Appl. No.: 15/671,465

(22) Filed: Aug. 8, 2017

(65) Prior Publication Data

US 2019/0046562 A1 Feb. 14, 2019

(51) Int. Cl.

*A61K 33/00* (2006.01)
*A61K 47/02* (2006.01)
*A61K 9/00* (2006.01)
*A61K 31/352* (2006.01)
*A61K 45/06* (2006.01)

(52) U.S. Cl.

CPC ............ *A61K 33/00* (2013.01); *A61K 9/0019* (2013.01); *A61K 9/0053* (2013.01); *A61K 9/0095* (2013.01); *A61K 31/352* (2013.01); *A61K 45/06* (2013.01); *A61K 47/02* (2013.01)

(58) Field of Classification Search

None

See application file for complete search history.

(56) References Cited

U.S. PATENT DOCUMENTS 3,074,776 A 1/1963 Ryan et al.
3,425,859 A 2/1969 Steigelman et al.
3,655,448 A 4/1972 Herbert
3,963,460 A 6/1976 Stumpf et al.
4,337,295 A 6/1982 Rittler et al.
5,009,901 A 4/1991 Byrne et al.
5,382,714 A 1/1995 Khachik
5,648,564 A 7/1997 Ausich et al.
5,803,301 A 9/1998 Sato et al.
5,827,790 A 10/1998 Evans et al.
5,888,357 A 3/1999 Mitsumori et al.
6,017,599 A 1/2000 Sakamoto et al.
6,173,790 B1 1/2001 Russwurm et al.
7,189,330 B2 3/2007 Hayashi et al.
7,560,091 B2 7/2009 Hayashi et al.
8,309,149 B2 11/2012 Yokoyama
8,518,225 B2 8/2013 Sumita et al.
8,574,503 B2 11/2013 Satoh et al.
8,663,444 B2 3/2014 Nabeshima
8,852,660 B2 10/2014 Miljkovic
8,887,625 B2 11/2014 Satoh et al.
8,974,646 B2 3/2015 Park et al.
9,050,278 B2 6/2015 Ohta et al.
9,120,672 B2 9/2015 Satoh et al.
9,144,581 B2 9/2015 Miljkovic
9,149,774 B2 10/2015 Satoh et al.
9,511,331 B2 12/2016 Igarashi
9,857,342 B2 1/2018 Tata
10,076,540 B1 9/2018 Perricone
10,155,010 B1 12/2018 Perricone
2002/0150657 A1 10/2002 Fan et al.
2002/0162458 A1 11/2002 Farr et al.
2005/0129621 A1 6/2005 Davies et al.
2005/0224996 A1 10/2005 Yoshida
2007/0017801 A1 1/2007 Fukui et al.
2007/0158449 A1 7/2007 Hoffmann et al.
2008/0311225 A1 12/2008 Shiga
2009/0035833 A1 2/2009 Ohta et al.
2010/0008849 A1 1/2010 Martin
2010/0008850 A1 1/2010 Martin
2010/0111830 A1 5/2010 Boyden et al.
2010/0163226 A1 7/2010 Zornes
2010/0233231 A1 9/2010 Labrecque et al.
2011/0111048 A1 5/2011 Satoh et al.
2011/0151058 A1 6/2011 Yoshida
2011/0155177 A1 6/2011 Tamura et al.
2011/0274922 A1 11/2011 Yasue et al.

(Continued)

FOREIGN PATENT DOCUMENTS

CA 2962376 A1 3/2016
CN 201347236 Y 11/2009

(Continued)

OTHER PUBLICATIONS

Gharib, CR Acad Sci Paris, Life Sciences, 324, 2001 (Year: 2001).*

(Continued)

*Primary Examiner* — Robert A Wax
*Assistant Examiner* — William Craigo
(74) *Attorney, Agent, or Firm* — Wolf, Greenfield & Sacks, P.C.

(57) ABSTRACT

Embodiments described herein generally relate to medicinal compositions (e.g., compositions comprising an active pharmaceutical agent) such as those comprising liquid hydrogen and/or hydrogen gas. In certain embodiments, the composition comprises hydrogen and/or noble gas(es) in a medicinal composition, for example, within the aqueous phase (e.g., dissolved). For example, in some cases, the medicinal composition may comprise an active pharmaceutical ingredient and hydrogen ($H_2$) and/or noble gas(es). The noble gas may be, for example, xenon, argon, or the like. In some embodiments, the hydrogen and/or the noble gas(es) may infuse with the composition (e.g., such that at least a portion of the hydrogen gas and/or noble gas(es) is dissolved within the composition). Such compositions comprising hydrogen gas and/or noble gas(es) may be useful, for example, for the treatment of animal and human diseases, for improvement in athletic performance, for the enhancement of the overall health of a subject, or the like. Such compositions and/or liquids described herein may be administered (e.g., orally, intravenously, inhaled) to/by a subject.

7 Claims, 3 Drawing Sheets

(56) References Cited

U.S. PATENT DOCUMENTS

2012/0070540 A1 3/2012 Igarashi
2012/0087990 A1 4/2012 Shiga et al.
2012/0107300 A1* 5/2012 Schirripa .............. A61K 31/14 424/94.65
2012/0289559 A1 11/2012 Niwa et al.
2013/0108515 A1* 5/2013 Satoh ....................... C01B 3/08 422/162
2013/0122150 A1 5/2013 Kim et al.
2014/0010483 A1 1/2014 Shih et al.
2014/0027384 A1 1/2014 Little et al.
2014/0151321 A1 6/2014 Chang et al.
2014/0247689 A1 9/2014 Wang et al.
2014/0363361 A1 12/2014 Wang et al.
2015/0079197 A1* 3/2015 Kazama ................ A61K 31/05 424/600
2015/0104698 A1 4/2015 Fung et al.
2015/0121807 A1* 5/2015 Taber ..................... B65B 31/08 53/431
2015/0197657 A1 7/2015 Niederst et al.
2015/0197863 A1 7/2015 Kim et al.
2015/0239760 A1 8/2015 Kim et al.
2015/0284280 A1 10/2015 Huang et al.
2016/0030387 A1* 2/2016 Winnicki .............. A61K 9/127 424/450
2016/0030470 A1 2/2016 Huang et al.
2016/0054278 A1 2/2016 Tata
2016/0207765 A1 7/2016 Takehara
2016/0263535 A1 9/2016 Lin
2016/0353782 A1 12/2016 Ruppman
2017/0043932 A1 2/2017 Byun et al.
2017/0080022 A1 3/2017 Levy
2018/0338510 A1 11/2018 Perricone
2018/0338511 A1 11/2018 Perricone
2018/0338995 A1 11/2018 Perricone
2019/0046561 A1 2/2019 Perricone
2019/0046754 A1 2/2019 Perricone
2019/0046755 A1 2/2019 Perricone
2019/0047729 A1 2/2019 Perricone

FOREIGN PATENT DOCUMENTS

CN 101961051 A 2/2011
CN 105476480 A 4/2016
CN 205312023 U 6/2016
CN 106721799 A 5/2017
DE 3048433 A1 7/1982
EP 0767632 A1 4/1997
EP 2583937 A1 4/2013
GB 1014712 A 12/1965
GB 2042398 A 9/1980
GB 201111619 A 5/2013
JP 8056632 3/1996
JP 2002301483 A 10/2002
JP 2004351399 A 12/2004
JP 3606466 B1 1/2005
JP 2007238100 A 9/2007
JP 2008110342 A 5/2008
JP 2008178769 A 8/2008
JP 2008239598 A 10/2008
JP 2008295436 A 12/2008
JP 4383317 B2 12/2009
JP 4573904 B1 11/2010
JP 2013126650 A 6/2013
JP 5699232 B1 4/2015
JP 5789907 B2 10/2015
KR 100678576 B1 10/2005
KR 20060035663 A 4/2006
KR 20160124638 A 10/2016
RU 95115488 A 9/1997
RU 123685 U1 1/2013
TW 316922 B 10/2005
TW 492296 U 12/2014
WO WO 2002/002409 A1 1/2002
WO WO 2008/029525 A1 3/2008
WO WO 2006/051588 A1 5/2008
WO WO 2008/072615 A1 6/2008
WO WO 2011/038799 A1 4/2011
WO WO 2012/073734 A1 6/2012
WO WO 2013/009928 A1 1/2013
WO WO 2014/145443 A2 9/2014
WO WO 2015/133409 A1 9/2015
WO WO 2015/175547 A1 11/2015
WO WO 2017/192755 A1 11/2017

OTHER PUBLICATIONS

[No Author Listed], 500ml Drinking Hydrogen Rich Water Generator with built in lithium battery fastest delivery and shipping. Ali Express. Retrieved from https://www.aliexpress.com/item/500ml-Drinking-Hydrogen-Rich-Water-Generator-with-bulit-in-lithium-battery-fastest-delivery-and-shipping/32729940876.html?aff_platform=aaf&cpt=1484687007133&sk=JEYRB2F&aff_trace_key=bc5bdfad4e864ea2910a88ec8daf3271-1484687007133-06041-JEYRB2F. Date accessed: Oct. 25, 2017. 3 pages.

[No Author Listed], Blue Mercury Product Information. Retrieved from http://www.bluemercury.co.jp/e/product_introduction.html. Date accessed: Oct. 25, 2017. 1 page.

[No Author Listed], H2 Hydrogen Water Pack. Retrieved from http://www.hydrogenwater-stick.com/. Date accessed: Oct. 25, 2017. 6 pages.

[No Author Listed], Liquid Nitrogen Dosing System: Standard Features. Inline Filling Systems. Retrieved from http://www.fillers.com/liquid-nitrogen-dosing-system/. Date accessed: Mar. 6, 2017. 2 pages.

[No Author Listed], Applications Vacuum Barrier Corporation. Retrieved from http://vacuumbarrier.com/applications/. Last Accessed: Mar. 6, 2017. 1 page.

[No Author Listed], What happens if you mix water with liquid hydrogen? Quora. Retreived from https://www.quora.com/What-happens-if-you-mix-water-with-liquid-hydrogen. Date accessed: Oct. 25, 2017. 2 pages.

Cleveland et al., Continuously Infusing Hyperpolarized 129Xe into Flowing Aqueous Solutions Using Hydrophobic Gas Exchange Membranes. J Phys Chem B. Sep. 17, 2009; 113(37):12489-12499.

Esencan et al., Xenon in medical area: emphasis on neuroprotection in hypoxia and anesthesia. Med Gas Res. Feb. 1, 2013;3(1):4. doi: 10.1186/2045-9912-3-4.

Harris et al., Neuroprotection against traumatic brain injury by xenon, but not argon, is mediated by inhibition at the N-methyl-D-aspartate receptor glycine site. Anesthesiology. Nov. 2013;119(5):1137-48. doi: 10.1097/ALN.0b013e3182a2a265.

Harris, Measuring out fluids microdrop by microdrop. Machine Design. Dec. 7, 2000. 8 pages.

Hiraoka et al., Studies on the properties and real existence of aqueous solution systems that are assumed to have antioxidant activities by the action of "active hydrogen." Journal of Health Sciences. 2004; 50(5):456-465.

Koh et al., Xenon gas as a performance-enhancing drug: doping or just hot air? Cycling Tips. Retrieved from https://cyclingtips.com/2014/03/xenon-gas-as-a-performance-enhancing-drug-doping-or-just-hot-air/. Date accessed: Oct. 25, 2017. 11 pages.

Kurita et al., Measurements of hydrogen permeation through fused silica and borosilicate glass by electrochemical pumping using oxide protonic conductor. Solic State Ionics. 2002;146:101-11.

Nicolson et al., Clinical Effects of Hydrogen Administration: From Animal and Human Diseases to Exercise Medicine. International Journal of Clinical Medicine. Jan. 2016;7(1):32-76.

Taleyarkhan, Modeling & Analysis of Liquid Deuterium-Water Reactions. Oak Ridge National Laboratory. 1995. 10 pages.

[No Author Listed], Alchemia Nova "Noble Gas Waters," pp. 1-3. http://www.alchemianova.com/articles/nobles.html, 20005. (Year: 2001)

[No Author Listed], Brown's Gas, How Much PPM of hydrogen will the Aquacure infuse into water? http://www.eagle-research.com/cms/faq/brown-gas/brown-gas-healthenhancement. (Year: 2005).

(56) References Cited

OTHER PUBLICATIONS

Ishibashi et al., Consumption of water containing a high concentration of molecular hydrogen reduces oxidative stress and disease activity in patients with rheumatoid arthritis: an open-label pilot study. Med Gas Res. Oct. 2, 2012;2(1):27. doi: 10.1186/2045-9912-2-27.
Kang et al., Effects of drinking hydrogen-rich water on the quality of life of patients treated with radiotherapy for liver tumors. Med Gas Res. Jun. 7, 2011;1(1):11. doi: 10.1186/2045-9912-1-11.
Verkhovskaya et al., Manufacturing the Technology of Xenon Containing Drinking Water and its Influence on Some Psychophysiological Characteristics of Man. Publicly disclosed on May 25-28, 2016.
International Search Report and Written Opinion for Application No. PCT/US2018/045538 dated Nov. 22, 2018.
[No Author Listed], Valspar Packaging. Aug. 3, 2016. Retrieved from https://www.youtube.com/watch?v=IzSxyJzMK34.
[No Author Listed], INERIS, Jun. 2017. Retrieved from https://substitution.ineris.fr/sites/substitution-portail/files/newsletter_sna_11_en_0.pdf.
Geueke, Dossier—Can Coatings. Dec. 2016. Retrieved from https://www.foodpackagingforum.org/fpf-2016/wp-content/uploads/2016/FPF_Dossier1 1_cancoatings-1.pdf.
Shen et al., A review of experimental studies of hydrogen as a new therapeutic agent in emergency and critical care medicine. Med Gas Res. Nov. 8, 2014;4:17. doi: 10.1186/2045-9912-4-17. eCollection 2014.
Soto et al., Evidence of Absence: Estrogenicity Assessment of a New Food-Contact Coating and the Bisphenol Used in Its Synthesis. Environ Sci Technol. Feb. 7, 2017;51(3):1718-1726. doi: 10.1021/acs.est.6b04704. Epub Jan. 18, 2017.
U.S. Appl. No. 15/834,263, filed Dec. 12, 2017, Perricone.
U.S. Appl. No. 15/986,885, filed May 23, 2018, Perricone.
U.S. Appl. No. 15/671,465, filed Aug. 8, 2017, Perricone.
International Preliminary Report on Patentability for Application No. PCT/US2018/045538 dated Feb. 20, 2020.
U.S. Appl. No. 15/671,391, filed Aug. 8, 2017, Perricone.
U.S. Appl. No. 15/671,403, filed Aug. 8, 2017, Perricone.
U.S. Appl. No. 16/687,613, filed Nov. 18, 2019, Perricone.

* cited by examiner

MEDICATION ENHANCEMENT USING HYDROGEN

FIELD OF THE INVENTION

The present invention generally relates to medicinal compositions, such as those comprising hydrogen and/or other gases.

BACKGROUND $H_2$ can be administered to a subject in the form of, for example, a gas, an infusion, a topical solution, or through the drinking of $H_2$-enriched water. Production of hydrogen-rich water has been accomplished by several methods, ranging from large-scale, but less self-stable, manufacturing techniques to small-volume single use devices for locally generating hydrogen gas.

SUMMARY OF THE INVENTION

The present invention generally relates to medicinal compositions, such as those comprising hydrogen and/or other gases. The subject matter of the present invention involves, in some cases, interrelated products, alternative solutions to a particular problem, and/or a plurality of different uses of one or more systems and/or articles.

In one aspect, compositions are provided. In some embodiments, the composition comprises an active pharmaceutical agent and greater than or equal to 0.1 mg and less than or equal to 5 mg liquid hydrogen.

In another aspect, methods are provided. In some embodiments, the method comprises introducing, into a composition comprising an active pharmaceutical agent, greater than or equal to 0.1 mg of liquid hydrogen and administering the composition to a subject.

Other advantages and novel features of the present invention will become apparent from the following detailed description of various non-limiting embodiments of the invention when considered in conjunction with the accompanying figures. In cases where the present specification and a document incorporated by reference include conflicting and/or inconsistent disclosure, the present specification shall control. If two or more documents incorporated by reference include conflicting and/or inconsistent disclosure with respect to each other, then the document having the later effective date shall control.

Figure 1:
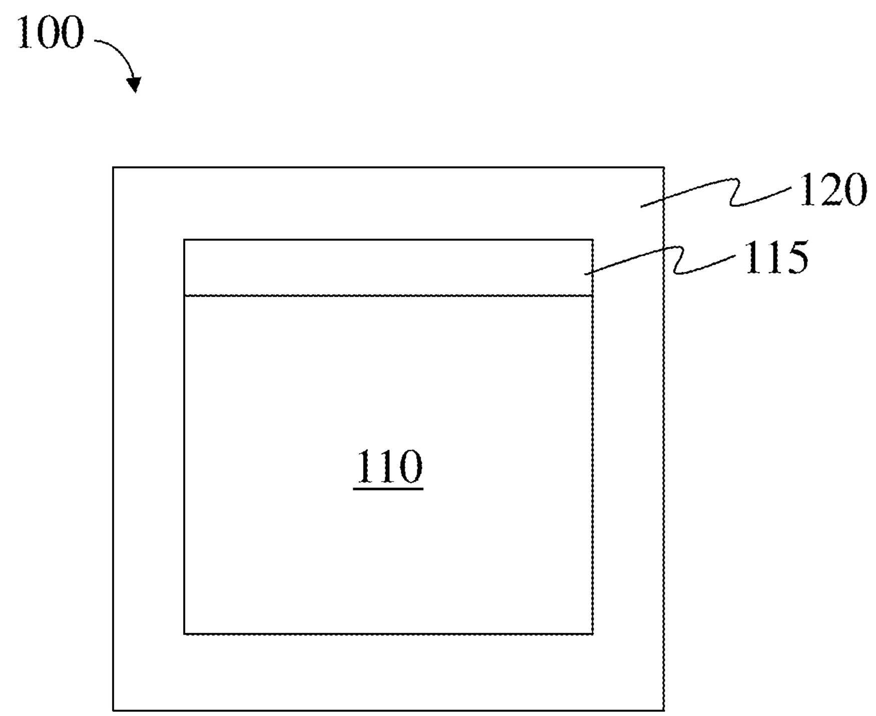
FIG. 1 shows a schematic drawing illustrating an article comprising a medicinal composition disposed within a container, according to one set of embodiments.

Other aspects, embodiments and features of the invention will become apparent from the following detailed description when considered in conjunction with the accompanying drawings. The accompanying figures are schematic and are not intended to be drawn to scale. For purposes of clarity, not every component is labeled in every figure, nor is every component of each embodiment of the invention shown where illustration is not necessary to allow those of ordinary skill in the art to understand the invention. All patent applications and patents incorporated herein by reference are incorporated by reference in their entirety. In case of conflict, the present specification, including definitions, will control.

DETAILED DESCRIPTION

Embodiments described herein generally relate to medicinal compositions (e.g., compositions comprising an active pharmaceutical agent) such as those comprising liquid hydrogen and/or hydrogen gas. In certain embodiments, the composition comprises hydrogen and/or noble gas(es) in a medicinal composition, for example, within the aqueous phase (e.g., dissolved). For example, in some cases, the medicinal composition may comprise an active pharmaceutical ingredient and hydrogen ($H_2$) and/or noble gas(es). The noble gas may be, for example, xenon, argon, or the like. In some embodiments, the hydrogen and/or the noble gas(es) may infuse with the composition (e.g., such that at least a portion of the hydrogen gas and/or noble gas(es) is dissolved within the composition). Such compositions comprising hydrogen gas and/or noble gas(es) may be useful, for example, for the treatment of animal and human diseases, for improvement in athletic performance, for the enhancement of the overall health of a subject, or the like. Such compositions and/or liquids described herein may be administered (e.g., orally, intravenously, inhaled) to/by a subject.

In some cases, the composition may be administered to a subject (e.g., administered to a subject to treat a disease, disorder, or other clinically recognized condition, or for prophylactic purposes). In certain embodiments, the article may be administered orally, intravenously, rectally, nasally (e.g., via a nasal spray, via a nasal dropper), or uretherally (e.g., via a catheter). In certain embodiments, the composition may be orally administered to a subject, (e.g., ingested or drunk by a subject, encapsulated in a pill (e.g., the composition is contained in a capsule such as a gel-capsule)). In certain embodiments, the composition may be consumed orally (e.g., eaten, drunk, swallowed, etc.).

Advantageously, the administration of a composition comprising hydrogen ($H_2$) and/or noble gas(es) and an active pharmaceutical agent to a subject as described herein may result in significantly higher uptake rates (e.g., a reduction in the amount of time before the subject exhibits an effect of the active pharmaceutical agent) as compared to administration of the active pharmaceutical agent alone. In some embodiments, the composition comprising hydrogen and/or noble gas(es) may advantageously permit lower concentrations (e.g., weight percent) of active pharmaceutical agents to be administered to a subject as compared to administration of the active pharmaceutical agent alone, while exhibiting substantially similar effects of the active pharmaceutical agent. By way of example, a subject administered a composition comprising a cannabinoid (e.g., tetrahydrocannabinol) and hydrogen may exhibit a psychotropic effect(s) within minutes (e.g., less than 5 minutes) as compared to administration of the same concentration of cannabinoid alone (e.g., greater than 30 minutes or more).

In some embodiments, the composition comprising hydrogen and an active pharmaceutical agent may have an uptake rate that is at least 2, at least 3, at least 5, at least 10, at least 20, at least 30, or at least 50 times the uptake rate of the active pharmaceutical agent alone by a subject. In certain embodiments, composition comprising hydrogen and an active pharmaceutical agent may have an uptake rate that is less than or equal to 100, less than or equal to 50, less than or equal to 30, less than or equal to 20, less than or equal to 10, less than or equal to 5, or less than or equal to 3 times the uptake rate of the active pharmaceutical agent alone by the subject. Combinations of the above-referenced ranges are also possible (e.g., at least 2 or less than or equal to 100 times). Other ranges are also possible. The uptake rate of a composition (or active pharmaceutical agent) may be determined by administering the composition (or active pharmaceutical agent) to a subject and determining the amount of time required to observe a pharmacological effect (e.g., a psychotropic effect, a reduction in disease and/or clinical symptom) of the active pharmaceutical agent on the subject.

According to some embodiments, the composition and methods described herein comprising one or more active pharmaceutical agents such as therapeutic, diagnostic, and/or enhancement agents, including but not limited to drugs, nutrients, microorganisms, in vivo sensors, and tracers. In some embodiments, the active pharmaceutical agent, is a therapeutic, nutraceutical, prophylactic or diagnostic agent. The active pharmaceutical agent may be present in solution (e.g., an aqueous solution), solid (e.g., powder), and/or gaseous form.

In an exemplary set of embodiments, the active pharmaceutical agent is a cannabinoid and/or derivative(s) thereof. Non-limiting examples of cannabinoids include tetrahydrocannabinol (THC), cannabidiol, cannabigerol, tetrahydrocannabivarin, cannabidivarin, and cannabichromene.

Active pharmaceutical agents can include, but are not limited to, any synthetic or naturally-occurring biologically active compound or composition of matter which, when administered to a subject (e.g., a human or nonhuman animal), induces a desired pharmacologic, immunogenic, and/or physiologic effect by local and/or systemic action. For example, useful or potentially useful within the context of certain embodiments are compounds or chemicals traditionally regarded as drugs, vaccines, and biopharmaceuticals, Certain such agents may include molecules such as proteins, peptides, hormones, nucleic acids, gene constructs, etc., for use in therapeutic, diagnostic, and/or enhancement areas, including, but not limited to medical or veterinary treatment, prevention, diagnosis, and/or mitigation of disease or illness (e.g., HMG co-A reductase inhibitors (statins) like rosuvastatin, nonsteroidal anti-inflammatory drugs like meloxicam, selective serotonin reuptake inhibitors like escitalopram, blood thinning agents like clopidogrel, steroids like prednisone, antipsychotics like aripiprazole and risperidone, analgesics like buprenorphine, antagonists like naloxone, montelukast, and memantine, cardiac glycosides like digoxin, alpha blockers like tamsulosin, cholesterol absorption inhibitors like ezetimibe, metabolites like colchicine, antihistamines like loratadine and cetirizine, opioids like loperamide, proton-pump inhibitors like omeprazole, antibiotics like doxycycline, ciprofloxacin, and azithromycin, anti-malarial agents, and synthroid/levothyroxine); substance abuse treatment (e.g., methadone and varenicline); family planning (e.g., hormonal contraception); psychotropic substances (e.g., cannabinoids); performance enhancement (e.g., stimulants like caffeine); and nutrition and supplements (e.g., protein, folic acid, calcium, iodine, iron, zinc, thiamine, niacin, vitamin C, vitamin D, and other vitamin or mineral supplements).

In certain embodiments, the active pharmaceutical agent is one or more specific therapeutic agents. As used herein, the term "therapeutic agent" or also referred to as a "drug" refers to an agent that is administered to a subject to treat a disease, disorder, or other clinically recognized condition, or for prophylactic purposes, and has a clinically significant effect on the body of the subject to treat and/or prevent the disease, disorder, or condition. Listings of examples of known therapeutic agents can be found, for example, in the United States Pharmacopeia (USP), Goodman and Gilman's The Pharmacological Basis of Therapeutics, 10th Ed., McGraw Hill, 2001; Katzung, B. (ed.) Basic and Clinical Pharmacology, McGraw-Hill/Appleton & Lange; 8th edition (Sep. 21, 2000); Physician's Desk Reference (Thomson Publishing), and/or The Merck Manual of Diagnosis and Therapy, 17th ed. (1999), or the 18th ed (2006) following its publication, Mark H. Beers and Robert Berkow (eds.), Merck Publishing Group, or, in the case of animals, The Merck Veterinary Manual, 9th ed., Kahn, C. A. (ed.), Merck Publishing Group, 2005; and "Approved Drug Products with Therapeutic Equivalence and Evaluations," published by the United States Food and Drug Administration (F.D.A.) (the "Orange Book"). Examples of drugs approved for human use are listed by the FDA under 21 C.F.R. §§ 330.5, 331 through 361, and 440 through 460, incorporated herein by reference; drugs for veterinary use are listed by the FDA under 21 C.F.R. §§ 500 through 589, incorporated herein by reference. In certain embodiments, the therapeutic agent is a small molecule. Exemplary classes of therapeutic agents include, but are not limited to, analgesics, anti-analgesics, anti-inflammatory drugs, antipyretics, antidepressants, anti-epileptics, antipsychotic agents, neuroprotective agents, anti-proliferatives, such as anti-cancer agents, antihistamines, antimigraine drugs, hormones, pro staglandins, antimicrobials (including antibiotics, antifungals, antivirals, antiparasitics), antimuscarinics, anxioltyics, bacteriostatics, immunosuppressant agents, sedatives, hypnotics, antipsychotics, bronchodilators, anti-asthma drugs, cardiovascular drugs, anesthetics, anti-coagulants, inhibitors of an enzyme, steroidal agents, steroidal or non-steroidal anti-inflammatory agents, corticosteroids, dopaminergics, electrolytes, gastro-intestinal drugs, muscle relaxants, nutritional agents, vitamins, parasympathomimetics, stimulants, anorectics and anti-narcoleptics.

Nutraceuticals such as vitamins, supplements such as calcium or biotin, or natural ingredients such as plant extracts or phytohormones, may also be present in the composition.

In certain embodiments, the composition (e.g., comprising hydrogen and/or noble gas(es) and a pharmaceutical agent(s)) may be configured to be administered (e.g., orally, intravenously, etc.) to a subject (e.g., in a clinical setting). In some embodiments, the composition may be administered orally.

In some embodiments, the composition comprising hydrogen and/or noble gases and a pharmaceutical agent(s) is an ingestible composition. One of ordinary skill in the art would understand that the term "ingestible" as used herein is not intended to encompass any and all substances and/or compositions that may be placed in a subject's body (e.g., via swallowing or drinking). Ingestible compositions are those that are edible, e.g., typically intended to be digested and absorbed by the body of the subject for e.g., nourishment, pleasure, therapeutic effect, and/or energy. In some embodiments, the ingestible composition is non-toxic, although those of ordinary skill in the art would understand that some ingestible compositions, such as therapeutic agents, may have some negligible level of toxicity but which provide a therapeutic benefit. By way of example, a stainless steel ball, while a capable of being swallowed by a subject, would not be considered an ingestible composition as e.g., it provides no nourishing, pleasure, or therapeutic effect on the subject. Similarly, antifreeze, while a liquid, would not be considered an ingestible composition (e.g., as it provides a detrimental effect on the body of the subject). By contrast, and by way of example without wishing to be limited by such, a liquid such as water or food such as pudding, which are generally consumed for nourishment and/or pleasure, would each be considered an ingestible composition.

For example, the composition comprising hydrogen and/or noble gases and an active pharmaceutical agent may comprise, for example, an ingestible composition including a liquid such as water (or other drinkable liquids), optionally with a variety of additives, such as sugar, electrolytes, caffeine, salt(s), flavoring, vitamins, herbs, amino acids, tea extracts, seed extracts, fruit extracts. The liquid may be any of a variety of drinkable liquids, such as a fruit juice or a juice-like beverage (e.g., powdered drinks such as Crystal Light®, Kool-Aid®, or the like), coffee, tea, a sports drink, an energy drink, soda pop, milk (e.g., cow's milk, goat's milk, sheep's milk, low-fat milk, whole milk, cream, chocolate milk), an alcoholic drink (e.g., mixed alcoholic beverages, wine, beer), or the like.

In some cases, the composition may be in the form of an intravenous fluid (e.g., saline, Ringer's lactate). In certain embodiments, the composition may be administered to a subject via injection (e.g., via syringe, needle, or the like).

In some cases, the hydrogen and/or noble gas(es) may be added to compositions such as nasal sprays, ear drops, eye drops, toothpastes, mouthwashes, and/or topical compositions.

In some embodiments, the composition may be configured to be administered to a subject topically (e.g., a topical composition). Non-limiting examples of topical compositions include topical solutions, cosmetics, creams (e.g., steroidal creams, antibiotic creams), foams, pastes, gels, lotions, soaps, jellies (e.g., petroleum jelly), lip balms, shampoos, and ointments.

In some embodiments, one or more additives may be present in the composition. Non-limiting examples of additives include sugar, electrolytes, caffeine, salt(s), flavoring, vitamins, herbs, amino acids, tea extracts, seed extracts, fruit extracts, and combinations thereof. The one or more additives may be present in any suitable amount. For example, in some embodiments, the additive is present in the composition in an amount of greater than or equal to 0.1 vol %, greater than or equal to 0.2 vol %, greater than or equal to 0.25 vol %, greater than or equal to 0.5 vol %, greater than or equal to 0.75 vol %, greater than or equal to 1 vol %, greater than or equal to 1.25 vol %, greater than or equal to 1.5 vol %, greater than or equal to 1.75 vol %, greater than or equal to 2 vol %, greater than or equal to 2.25 vol %, greater than or equal to 2.5 vol %, greater than or equal to 3 vol %, greater than or equal to 3.5 vol %, greater than or equal to 4 vol %, or greater than or equal to 4.5 vol % versus the total volume of the composition.

In certain embodiments, the additive is present in the composition in an amount less than or equal to 5 vol %, less than or equal to 4.5 vol %, less than or equal to 4 vol %, less than or equal to 3.5 vol %, less than or equal to 3 vol %, less than or equal to 2.5 vol %, less than or equal to 2.25 vol %, less than or equal to 2 vol %, less than or equal to 1.75 vol %, less than or equal to 1.5 vol %, less than or equal to 1.25 vol %, less than or equal to 1 vol %, less than or equal to 0.75 vol %, less than or equal to 0.5 vol %, less than or equal to 0.25 vol %, or less than or equal to 0.2 vol % versus the total volume of the composition. Combinations of the above-referenced ranges are also possible (e.g., greater than or equal to 0.1 vol % and less than or equal to 5 vol %). Other ranges are also possible.

In some embodiments, a composition comprises hydrogen, noble gas (e.g., liquid xenon), and one or more additives, in the ranges listed herein. In some cases, the remainder of the composition may be an active pharmaceutical agent and/or excipient (e.g., a liquid, a solvent, a bulking agents, a filler, a diluent, etc.).

In certain embodiments, an active pharmaceutical agent is present in the composition (e.g., the composition comprising hydrogen and/or a noble gas(es)) in an amount of greater than or equal to 1 wt %, greater than or equal to 2 wt %, greater than or equal to 5 wt %, greater than or equal to 10 wt %, greater than or equal to 15 wt %, greater than or equal to 20 wt %, greater than or equal to 25 wt %, greater than or equal to 30 wt %, greater than or equal to 35 wt %, greater than or equal to 40 wt %, greater than or equal to 45 wt %, greater than or equal to 50 wt %, greater than or equal to 55 wt %, greater than or equal to 60 wt %, greater than or equal to 65 wt %, greater than or equal to 70 wt %, greater than or equal to 75 wt %, greater than or equal to 80 wt %, greater than or equal to 85 wt %, greater than or equal to 90 wt %, greater than or equal to 91 wt %, greater than or equal to 92 wt %, greater than or equal to 93 wt %, greater than or equal to 94 wt %, greater than or equal to 95 wt %, greater than or equal to 96 wt %, greater than or equal to 97 wt %, greater than or equal to 98 wt %, greater than or equal to 99 wt %, greater than or equal to 99.5 wt %, or greater than or equal to 99.9 wt % versus the total composition weight. In some embodiments, the active pharmaceutical agent is present in an amount of less than or equal to 99.99 wt %, less than or equal to 99.9 wt %, less than or equal to 99.5 wt %, less than or equal to 99 wt %, less than or equal to 98 wt %, less than or equal to 97 wt %, less than or equal to 96 wt %, less than or equal to 95 wt %, less than or equal to 94 wt %, less than or equal to 93 wt %, less than or equal to 92 wt %, less than or equal to 91 wt %, less than or equal to 90 wt %, less than or equal to 85 wt %, less than or equal to 80 wt %, less than or equal to 75 wt %, less than or equal to 70 wt %, less than or equal to 65 wt %, less than or equal to 60 wt %, less than or equal to 55 wt %, less than or equal to 50 wt %, less than or equal to 45 wt %, less than or equal to 40 wt %, less than or equal to 35 wt %, less than or equal to 30 wt %, less than or equal to 25 wt %, less than or equal to 20 wt %, less than or equal to 15 wt %, less than or equal to 10 wt %, less than or equal to 5 wt %, or less than or equal to 2 wt % versus the total composition weight. Combinations of the above-referenced ranges are also possible (e.g., greater than or equal to 1 wt % and less than or equal to 99.99 wt %, greater than or equal to 1 wt % and less than or equal to 20 wt %, greater than or equal to 10 wt % and less than or equal to 50 wt %, greater than or equal to 25 wt % and less than or equal to 75 wt %, greater than or equal to 50 wtˆ and less than or equal to 99.99 wt %). Other ranges are also possible.

In some embodiments, the composition comprises hydrogen, a noble gas (e.g., xenon gas), and active pharmaceutical agent, in the ranges listed herein with the remainder of the composition being excipient. In certain embodiments, excipient is present in the composition in an amount of greater than or equal to 1 wt %, greater than or equal to 2 wt %, greater than or equal to 5 wt %, greater than or equal to 10 wt %, greater than or equal to 15 wt %, greater than or equal to 20 wt %, greater than or equal to 25 wt %, greater than or equal to 30 wt %, greater than or equal to 35 wt %, greater than or equal to 40 wt %, greater than or equal to 45 wt %, greater than or equal to 50 wt %, greater than or equal to 55 wt %, greater than or equal to 60 wt %, greater than or equal to 65 wt %, greater than or equal to 70 wt %, greater than or equal to 75 wt %, greater than or equal to 80 wt %, greater than or equal to 85 wt %, greater than or equal to 90 wt %, greater than or equal to 91 wt %, greater than or equal to 92 wt %, greater than or equal to 93 wt %, greater than or equal to 94 wt %, greater than or equal to 95 wt %, greater than or equal to 96 wt %, greater than or equal to 97 wt %, greater than or equal to 98 wt %, greater than or equal to 99 wt %, greater than or equal to 99.5 wt %, or greater than or equal to 99.9 wt % versus the total composition weight. In some embodiments, the excipient is present in an amount of less than or equal to 99.99 wt %, less than or equal to 99.9 wt %, less than or equal to 99.5 wt %, less than or equal to 99 wt %, less than or equal to 98 wt %, less than or equal to 97 wt %, less than or equal to 96 wt %, less than or equal to 95 wt %, less than or equal to 94 wt %, less than or equal to 93 wt %, less than or equal to 92 wt %, less than or equal to 91 wt %, less than or equal to 90 wt %, less than or equal to 85 wt %, less than or equal to 80 wt %, less than or equal to 75 wt %, less than or equal to 70 wt %, less than or equal to 65 wt %, less than or equal to 60 wt %, less than or equal to 55 wt %, less than or equal to 50 wt %, less than or equal to 45 wt %, less than or equal to 40 wt %, less than or equal to 35 wt %, less than or equal to 30 wt %, less than or equal to 25 wt %, less than or equal to 20 wt %, less than or equal to 15 wt %, less than or equal to 10 wt %, less than or equal to 5 wt %, or less than or equal to 2 wt % versus the total composition weight. Combinations of the above-referenced ranges are also possible (e.g., greater than or equal to 1 wt % and less than or equal to 99.99 wt %, greater than or equal to 1 wt % and less than or equal to 20 wt %, greater than or equal to 10 wt % and less than or equal to 50 wt %, greater than or equal to 25 wt % and less than or equal to 75 wt %, greater than or equal to 50 wtˆ and less than or equal to 99.99 wt %). Other ranges are also possible.

As described herein, in some embodiments, the composition may be used to improve the health of a subject. For example, the composition may reduce oxidative stress and/or reduce muscle fatigue (e.g., after exercise and/or athletic activity). In some cases, the composition may provide a psychotropic effect on the subject.

In certain embodiments, the composition may improve a subject's overall well-being including, for example, a feeling of increased energy levels, hastened recovery after exercise, improved memory, increased strength, and/or reduced tiredness. In some cases, the composition may be particularly delectable to the subject. In addition, in some cases, the composition may be used to treat a disease, disorder, or other clinically recognized condition, or for prophylactic purposes, or for providing physiological benefits, and has a clinically significant effect on the body of the subject to treat and/or prevent the disease, disorder, or condition, and/or has a clinically significant effect on the subject's physiology. In other embodiments, the composition may provide performance enhancement to a subject while, for example, exercising and/or performing athletic activities.

In such embodiments in which the composition is administered to a subject, the composition may comprise hydrogen in an amount of greater than or equal to greater than or equal to 0.1 ppm and less than or equal to 5 ppm and xenon gas (and/or other noble gases) in an amount of greater than or equal to 1 ppm and less than or equal to 20 ppm.

In some embodiments, the composition may be administered intravenously. In some such embodiments, the composition comprises hydrogen in an amount of greater than or equal to greater than or equal to 0.1 ppm and less than or equal to 5 ppm and xenon gas (and/or other noble gases) in an amount of greater than or equal to 1 ppm and less than or equal to 20 ppm.

Without wishing to be bound by any theory, while hydrogen, xenon and/or other noble gases may not be directly involved in any chemical reactions, such gases may participate in physical interactions within a subject (for example, by blocking receptors, creating size exclusion effects, and/or by competing with proteins), thereby resulting in various biological effects. This may be useful, for example, for the treatment of animal and human diseases, for improvement in athletic performance, for the enhancement of the overall health of a subject, or the like.

For example, in one set of embodiments, hydrogen may be used to increase the uptake rate of a particular active pharmaceutical agent.

In another set of embodiments, a noble gas such as xenon may be used to induce cardioprotection and/or neuroprotection through a variety of mechanisms. In certain cases, a composition as described herein can be used to treat conditions such as ischemia, e.g., partial ischemia or restriction in blood supply to tissues. For instance, a composition may be administered to a subject, e.g., on a regular basis as discussed herein, to protect neural and/or cardiac function. Without wishing to be bound by any theory, it is believed that xenon may affect $Ca^{2+}$, $K^+$, KATP\HIF, and/or NMDA antagonism; xenon may also activate PKC-epsilon, p38-MAPK, ATP-sensitive potassium channel, and/or hypoxia inducible factor 1 alpha (HIF1a), thereby allowing cardioprotective and/or neuroprotective effects to occur.

In another set of embodiments, xenon may be used to increase production of erythropoietin. This may be useful, for example, to increase red blood cells, e.g., to treat anemic subjects, or improve athletic performance. Without wishing to be bound by any theory, it is believed that xenon may enhance production of HIF1a, which is a transcription factor able to respond to hypoxic conditions. Accordingly, in some embodiments, a composition as described herein can be used to treat anemia or other conditions in a subject. In another set of embodiments, a composition as described herein may be used to increase a subject's physical energy levels, e.g., for improvement in athletic performance.

In addition, in low doses, xenon may cause certain analgesic effects, which may facilitate improved athletic performance in some cases (e.g., due to lower or reduced pain). For example, xenon may inhibit nicotinic acetylcholine alpha-4-beta-2 ($\alpha_4\beta_2$) receptors, plasma membrane $Ca^{2+}$ ATPase, and/or the serotonin 5-HT3 receptor. Xenon may also be an antagonist of high-affinity glycine-site NMDA, or it may activate the two-pore domain potassium channel TREK-1.

In some cases, xenon and other and other noble gases may exhibit synergistic effects with hydrogen ($H_2$), e.g., for certain applications such as for the treatment of animal and human diseases, for improvement in athletic performance, for the enhancement of the overall health of a subject, or the like.

Hydrogen may act within the body as an antioxidant. In some cases, hydrogen may be used to treat various oxidative stress conditions, for example, as an antioxidant, or by interaction with proteins such as NRF2. For example, strenuous exercise may cause oxidative stresses, e.g., due to muscle fatigue. Hydrogen may accordingly be used in some embodiments to treat athletes and improve athletic performance. Thus, in some cases, compositions such as those discussed herein, e.g., containing hydrogen and/or xenon (and/or other noble gases) may be provided to a subject to enhance athletic performance.

In addition, in some cases, hydrogen may be used to treat oxidative stress diseases and conditions such as smoking, exposure to ultraviolet rays, air pollution, aging, physical or psychological stress, cancer, or the aging process. Xenon (and/or other noble gases) may facilitate treatment by increasing red blood cell levels, e.g., as discussed herein. In addition, hydrogen may also exhibit other effects, such as anti-inflammatory properties, that may be useful in conjunction with xenon and/or other noble gases.

In certain embodiments of the invention, the administration of various compositions of the invention may be designed so as to result in sequential exposures to the composition over a certain time period, for example, hours, days, weeks, months, or years. This may be accomplished, for example, by repeated administrations of a composition of the invention by one or more of the methods described herein. In some cases, compositions may be applied to the subject on a relatively regular or periodic basis; e.g., a subject may drink a container each day, or a two, three, four, or more containers a day, or a container every other day, every third day, every fourth day, etc. Somewhat more irregular schedules are also possible (e.g., a regular number of containers per week or per month, etc.).

Thus, the compositions of the present invention may be administered in multiple doses over extended period of time. For any composition described herein the therapeutically effective amount can be initially determined from animal models. The applied dose can be adjusted based on the relative bioavailability and potency of the administered composition. Adjusting the dose to achieve maximal efficacy based on the methods described above and other methods as are well-known in the art is well within the capabilities of the ordinarily skilled artisan.

When administered to a subject, effective amounts will depend on the particular condition being treated and the desired outcome. A therapeutically effective dose may be determined by those of ordinary skill in the art, for instance, employing factors such as those described herein and using no more than routine experimentation.

In administering the compositions of the invention to a subject, dosing amounts, dosing schedules, routes of administration, and the like may be selected so as to affect known activities of these compositions. Dosages may be estimated based on the results of experimental models, optionally in combination with the results of assays of compositions of the present invention. Dosage may be adjusted appropriately to achieve desired drug levels, local or systemic, depending upon the mode of administration. The doses may be given in one or several administrations per day. Multiple doses per day are also contemplated in some cases to achieve appropriate systemic levels of the composition within the subject or within the active site of the subject.

The dosage may be given in some cases at the maximum amount while avoiding or minimizing any potentially detrimental side effects within the subject. The dosage of the composition that is actually administered is dependent upon factors such as the final concentration desired at the active site, the method of administration to the subject, the efficacy of the composition, the longevity of the composition within the subject, the timing of administration, the effect of concurrent treatments (e.g., as in a cocktail), etc. The dose delivered may also depend on conditions associated with the subject, and can vary from subject to subject in some cases. For example, the age, sex, weight, size, environment, physical conditions, or current state of health of the subject may also influence the dose required and/or the concentration of the composition. Variations in dosing may occur between different individuals or even within the same individual on different days. It may be preferred that a maximum dose be used, that is, the highest safe dose according to sound medical judgment. Preferably, the dosage form is such that it does not substantially deleteriously affect the subject.

Administration of the composition can be alone, or in combination with other therapeutic agents and/or compositions. In certain embodiments of the invention, a composition can be combined with a suitable pharmaceutically acceptable carrier (i.e. excipient), for example, within a suitable liquid. In general, pharmaceutically acceptable carriers suitable for use in the invention are well-known to those of ordinary skill in the art. As used herein, a "pharmaceutically acceptable carrier" refers to a non-toxic material that does not significantly interfere with the effectiveness of the biological activity of the active composition(s) to be administered, but is used as a formulation ingredient, for example, to stabilize or protect the active composition(s) within the composition before use. The carrier may include one or more compatible solid or liquid fillers, diluents or encapsulating substances which are suitable for administration to a human or other vertebrate animal. The term "carrier" denotes an organic or inorganic ingredient, which may be natural or synthetic, with which one or more compositions of the invention are combined to facilitate the application of the composition. The carrier may be co-mingled or otherwise mixed with one or more compositions of the present invention, and with each other, in a manner such that there is no interaction which would substantially impair the desired pharmaceutical efficacy. Those skilled in the art will know of suitable carriers, such as saline, or will be able to ascertain such, using only routine experimentation.

The formulations of the invention are administered in pharmaceutically acceptable solutions, which may routinely contain pharmaceutically acceptable concentrations of salt, buffering agents, preservatives, compatible carriers, adjuvants, emulsifiers, diluents, excipients, chelating agents, fillers, drying agents, antioxidants, antimicrobials, preservatives, binding agents, bulking agents, silicas, solubilizers, stabilizers and optionally other therapeutic ingredients, that may be used with the active composition. For example, if the formulation is a liquid, the carrier may be a solvent, partial solvent, or non-solvent, and may be aqueous or organically based. Examples of suitable formulation ingredients include diluents such as calcium carbonate, sodium carbonate, lactose, kaolin, calcium phosphate, or sodium phosphate; granulating and disintegrating agents such as corn starch or algenic acid; binding agents such as starch, gelatin or acacia; lubricating agents such as magnesium stearate, stearic acid, or talc; time-delay materials such as glycerol monostearate or glycerol distearate; suspending agents such as sodium carboxymethylcellulose, methylcellulose, hydroxypropylmethylcellulose, sodium alginate, polyvinylpyrrolidone; dispersing or wetting agents such as lecithin or other naturally-occurring phosphatides; thickening agents such as cetyl alcohol or beeswax; buffering agents such as acetic acid and salts thereof, citric acid and salts thereof, boric acid and salts thereof, or phosphoric acid and salts thereof; or preservatives such as benzalkonium chloride, chlorobutanol, parabens, or thimerosal. Suitable carrier concentrations can be determined by those of ordinary skill in the art, using no more than routine experimentation. The compositions of the invention may be formulated into preparations in solid, semi-solid, liquid or gaseous forms such as tablets, capsules, elixirs, powders, granules, ointments, solutions, depositories, inhalants or injectables. Those of ordinary skill in the art will know of other suitable formulation ingredients, or will be able to ascertain such, using only routine experimentation.

Suitable buffering agents include: acetic acid and a salt (1-2% w/v); citric acid and a salt (1-3% w/v); boric acid and a salt (0.5-2.5% w/v); and phosphoric acid and a salt (0.8-2% w/v). Suitable preservatives include benzalkonium chloride (0.003-0.03% w/v); chlorobutanol (0.3-0.9% w/v); parabens (0.01-0.25% w/v) and thimerosal (0.004-0.02% w/v).

Preparations include sterile aqueous or non-aqueous solutions, suspensions and emulsions, which can be isotonic with the blood of the subject in certain embodiments. Examples of non-aqueous solvents are polypropylene glycol, polyethylene glycol, vegetable oil such as olive oil, sesame oil, coconut oil, arachis oil, peanut oil, mineral oil, injectable organic esters such as ethyl oleate, or fixed oils including synthetic mono or di-glycerides. Aqueous carriers include water, alcoholic/compositions, emulsions or suspensions, including saline and buffered media. Parenteral vehicles include sodium chloride solution, 1,3-butandiol, Ringer's dextrose, dextrose and sodium chloride, lactated Ringer's or fixed oils. Intravenous vehicles include fluid and nutrient replenishers, electrolyte replenishers (such as those based on Ringer's dextrose), and the like. Preservatives and other additives may also be present such as, for example, antimicrobials, antioxidants, chelating agents and inert gases and the like. Those of skill in the art can readily determine the various parameters for preparing and formulating the compositions of the invention without resort to undue experimentation.

The present invention also provides any of the above-mentioned compositions in kits, optionally including instructions for use of the composition for the treatment of a condition discussed herein. That is, the kit can include a description of use of the composition for participation in any biological or chemical mechanism disclosed herein associated with a condition discussed herein. The kit can include a description of use of the compositions as discussed herein. The kit also can include instructions for use of a combination of two or more compositions of the invention, or instruction for use of a combination of a composition of the invention and one or more other compositions. Instructions also may be provided for administering the composition by any suitable technique as previously described, for example, orally, intravenously, pump or implantable delivery device, or via another known route of drug delivery.

The kits described herein may also contain one or more containers, which may contain the composition and other ingredients as previously described. The kits also may contain instructions for mixing, diluting, and/or administrating the compositions of the invention in some cases. The kits also can include other containers with one or more solvents, surfactants, preservative and/or diluents (e.g., normal saline (0.9% NaCl), or 5% dextrose) as well as containers for mixing, diluting or administering the components in a sample or to a subject in need of such treatment.

The compositions of the kit may be provided as any suitable form, for example, as liquid solutions. In embodiments where liquid forms of the composition are used, the liquid form may be concentrated or ready to use. The solvent will depend on the composition and the mode of use or administration. Suitable solvents for drug compositions are well known, for example as previously described, and are available in the literature. The solvent will depend on the composition and the mode of use or administration.

Hydrogen may be present within the composition in any suitable amount. In some embodiments, greater than or equal to 0.1 mg, greater than or equal to 0.2 mg, greater than or equal to 0.3 mg, greater than or equal to 0.4 mg, greater than or equal to 0.5 mg, greater than or equal to 0.6 mg, greater than or equal to 0.7 mg, greater than or equal to 0.8 mg, greater than or equal to 0.9 mg, greater than or equal to 1 mg, greater than or equal to 1.1 mg, greater than or equal to 1.2 mg, greater than or equal to 1.25 mg, greater than or equal to 1.3 mg, greater than or equal to 1.4 mg, greater than or equal to 1.5 mg, greater than or equal to 1.6 mg, greater than or equal to 1.7 mg, greater than or equal to 1.75 mg, greater than or equal to 1.8 mg, greater than or equal to 1.9 mg, greater than or equal to 2 mg, greater than or equal to 2.25 mg, greater than or equal to 2.5 mg, greater than or equal to 2.75 mg, greater than or equal to 3 mg, greater than or equal to 3.25 mg, greater than or equal to 3.5 mg, greater than or equal to 3.75 mg, greater than or equal to 4 mg, greater than or equal to 4.25 mg, greater than or equal to 4.5 mg, or greater than or equal to 4.75 mg of hydrogen is present per liter of composition.

In certain embodiments, the hydrogen is present in the composition in an amount of less than or equal to 5 mg, less than or equal to 4.75 mg, less than or equal to 4.5 mg, less than or equal to 4.25 mg, less than or equal to 4 mg, less than or equal to 3.75 mg, less than or equal to 3.5 mg, less than or equal to 3.25 mg, less than or equal to 3 mg, less than or equal to 2.75 mg, less than or equal to 2.5 mg, less than or equal to 2.25 mg, less than or equal to 2 mg, less than or equal to 1.9 mg, less than or equal to 1.8 mg, less than or equal to 1.75 mg, less than or equal to 1.7 mg, less than or equal to 1.6 mg, less than or equal to 1.5 mg, less than or equal to 1.4 mg, less than or equal to 1.3 mg, less than or equal to 1.25 mg, less than or equal to 1.2 mg, less than or equal to 1.1 mg, less than or equal to 1 mg, less than or equal to 0.9 mg, less than or equal to 0.8 mg, less than or equal to 0.7 mg, less than or equal to 0.6 mg, less than or equal to 0.5 mg, less than or equal to 0.4 mg, less than or equal to 0.3 mg, or less than or equal to 0.2 mg of hydrogen per liter of composition. Combinations of the above-referenced ranges are also possible (e.g., greater than or equal to 0.1 mg and less than or equal to 5 mg, greater than or equal to 1.5 mg and less than or equal to 2 mg per liter of composition).

In some embodiments, the container has a particular pressure that may be greater than atmospheric pressure. The pressure may be created within the container using any of a variety of gases, including air, nitrogen, carbon dioxide, water vapor, hydrogen gas, one or more noble gases (such as xenon), or the like, as well as combinations of these and/or other suitable gases. For example, liquid hydrogen and/or liquid noble gases may be introduced into the container (e.g., added to the composition disposed with the container) such that upon phase change of the liquid hydrogen and/or liquid noble gases into a gaseous phase, the pressure inside the container increases. Such gases may be at equilibrium with the liquid within the container. In addition, in some cases, one or more of the gases may be present in an amount such that at equilibrium, those gases are dissolved within the liquid, for example, at saturation concentrations.

For example, in certain embodiments, the container contains a pressure (e.g., is pressurized to a pressure of) at least 1 psi (1 psi is about 6894.757 Pa), at least 2 psi, at least 3 psi, at least 5 psi, at least 7 psi, at least 10 psi, at least 12 psi, at least 15 psi, at least 18 psi, at least 20 psi, at least 25 psi, at least 30 psi, at least 35 psi, at least 40 psi, or at least 45 psi greater than atmospheric pressure. In some embodiments, the container contains a pressure of less than or equal to 50 psi, less than or equal to 45 psi, less than or equal to 40 psi, less than or equal to 35 psi, less than or equal to 30 psi, less than or equal to 25 psi, less than or equal to 20 psi, less than or equal to 18 psi, less than or equal to 15 psi, less than or equal to 12 psi, less than or equal to 10 psi, less than or equal to 7 psi, less than or equal to 5 psi, less than or equal to 3 psi, or less than or equal to 2 psi greater than atmospheric pressure. Combinations of the above-referenced ranges are also possible (e.g., at least 1 psi and less than or equal to 50 psi greater than atmospheric pressure). Other ranges are also possible.

Those of ordinary skill in the art would be capable of selecting suitable amounts of liquid hydrogen and/or liquid noble gases to introduce to the container, based upon the teachings of this specification, such that the container is pressurized to a pressure in one or more ranges described above.

In some embodiments, the article comprises a gaseous headspace (e.g., a gaseous headspace present within the container). The gaseous headspace may comprise a variety of gases, such as oxygen, air, noble gases, or the like. For example, referring again to FIG. 1, in some cases, article 100 comprises gaseous headspace 115. The article may comprise any suitable amount of headspace within the container. In some embodiments, the headspace occupies greater than or equal to 0.1 vol %, greater than or equal to 0.2 vol %, greater than or equal to 0.25 vol %, greater than or equal to 0.5 vol %, greater than or equal to 0.75 vol %, greater than or equal to 1 vol %, greater than or equal to 1.25 vol %, greater than or equal to 1.5 vol %, greater than or equal to 1.75 vol %, greater than or equal to 2 vol %, greater than or equal to 2.25 vol %, greater than or equal to 2.5 vol %, greater than or equal to 3 vol %, greater than or equal to 3.5 vol %, greater than or equal to 4 vol %, or greater than or equal to 4.5 vol % of the volume contained by the container. In certain embodiments, the headspace occupies less than or equal to 5 vol %, less than or equal to 4.5 vol %, less than or equal to 4 vol %, less than or equal to 3.5 vol %, less than or equal to 3 vol %, less than or equal to 2.5 vol %, less than or equal to 2.25 vol %, less than or equal to 2 vol %, less than or equal to 1.75 vol %, less than or equal to 1.5 vol %, less than or equal to 1.25 vol %, less than or equal to 1 vol %, less than or equal to 0.75 vol %, less than or equal to 0.5 vol %, less than or equal to 0.25 vol %, or less than or equal to 0.2 vol % of the volume contained by the container. Combinations of the above-referenced ranges are also possible (e.g., greater than or equal to 0.1 vol % and less than or equal to 5 vol %). Other ranges are also possible.

For example, in some embodiments, the headspace comprises greater than or equal to 0.00001 vol %, greater than or equal to 0.00005 vol %, greater than or equal to 0.0001 vol %, greater than or equal to 0.0005 vol %, greater than or equal to 0.001 vol %, greater than or equal to 0.005 vol %, greater than or equal to 0.01 vol %, greater than or equal to 0.05 vol %, greater than or equal to 0.1 vol %, greater than or equal to 0.5 vol %, greater than or equal to 1 vol %, greater than or equal to 2 vol %, greater than or equal to 5 vol %, greater than or equal to 10 vol %, greater than or equal to 20 vol %, greater than or equal to 30 vol %, greater than or equal to 40 vol %, greater than or equal to 50 vol %, or greater than or equal to 60 vol % xenon gas (and/or other noble gases) versus the total volume of the headspace. In certain embodiments, xenon gas (and/or other noble gases) is present in the headspace in an amount less than or equal to 70 vol %, less than or equal to 60 vol %, less than or equal to 50 vol %, less than or equal to 40 vol %, less than or equal to 30 vol %, less than or equal to 20 vol %, less than or equal to 10 vol %, less than or equal to 5 vol %, less than or equal to 2 vol %, less than or equal to 1 vol %, less than or equal to 0.5 vol %, less than or equal to 0.1 vol %, less than or equal to 0.05 vol %, less than or equal to 0.01 vol %, less than or equal to 0.005 vol %, less than or equal to 0.001 vol %, less than or equal to 0.0005 vol %, less than or equal to 0.0001 vol %, or less than or equal to 0.00005 vol % versus the total volume of the headspace. Combinations of the above-referenced ranges are also possible (e.g., greater than or equal to 0.00001 vol % and less than or equal to 10 vol %). Other ranges are also possible.

In certain embodiments, the headspace comprises greater than or equal to 0.00001 vol %, greater than or equal to 0.00005 vol %, greater than or equal to 0.0001 vol %, greater than or equal to 0.0005 vol %, greater than or equal to 0.001 vol %, greater than or equal to 0.005 vol %, greater than or equal to 0.01 vol %, greater than or equal to 0.05 vol %, greater than or equal to 0.1 vol %, greater than or equal to 0.5 vol %, greater than or equal to 1 vol %, greater than or equal to 2 vol %, or greater than or equal to 5 vol % hydrogen gas versus the total volume of the headspace. In certain embodiments, hydrogen gas is present in the headspace in an amount less than or equal to 10 vol %, less than or equal to 5 vol %, less than or equal to 2 vol %, less than or equal to 1 vol %, less than or equal to 0.5 vol %, less than or equal to 0.1 vol %, less than or equal to 0.05 vol %, less than or equal to 0.01 vol %, less than or equal to 0.005 vol %, less than or equal to 0.001 vol %, less than or equal to 0.0005 vol %, less than or equal to 0.0001 vol %, or less than or equal to 0.00005 vol % versus the total volume of the headspace. Combinations of the above-referenced ranges are also possible (e.g., greater than or equal to 0.00001 vol % and less than or equal to 10 vol %). Other ranges are also possible.

In one set of embodiments, the liquid within the sealed container fills greater than or equal to 50 vol %, greater than or equal to 75 vol %, greater than or equal to 80 vol %, greater than or equal to 85 vol %, greater than or equal to 90 vol %, greater than or equal to 92 vol %, greater than or equal to 95 vol %, greater than or equal to 98 vol %, greater than or equal to 99 vol %, greater than or equal to 99.5 vol %, or greater than or equal to 99.9 vol % of the volume of the sealed container. In some cases, the volume of the liquid may be less than or equal to 99.99 vol %, less than or equal to 99.9 vol %, less than or equal to 99.5 vol %, less than or equal to 99 vol %, less than or equal to 98 vol %, less than or equal to 95 vol %, less than or equal to 92 vol %, less than or equal to 90 vol %, less than or equal to 85 vol %, less than or equal to 80 vol %, or less than or equal to 75 vol % of the volume of the sealed container. Combinations of the above-referenced ranges are also possible (e.g., greater than or equal to 50 vol % and less than or equal to 99.99 vol %).

Some embodiments relate to introducing liquid hydrogen ($H_2$) and/or a liquid noble gas(es) into a composition and/or a container comprising a composition such as described herein, and optionally sealing the container. The liquid hydrogen and/or other gases may be kept liquid by keeping them at relatively cold temperatures, e.g., at temperatures below their respective boiling points. In certain embodiments, after introduction into a container, the liquid hydrogen and/or liquid noble gas(es) change phase into gaseous phase, such that the contents (e.g., the composition, hydrogen gas, liquid noble gas(es), and/or any additives) contained within the sealed container are pressurized, e.g., as one or more of the liquids become gaseous or warms to a temperature greater than their respective boiling points. Advantageously, such containers described herein may provide liquids containing hydrogen and a noble gas that are shelf-stable (e.g., maintain a relatively stable concentration of hydrogen and/or noble gas(es)) for relatively long periods of time (e.g., at least 7 days). In some cases, such gases may be at equilibrium with being dissolved in the liquid phase.

In certain embodiments, upon introduction of the liquid hydrogen and/or liquid noble gas(es) into a composition and/or a container comprising the composition, the composition comprising hydrogen and/or noble gas(es) may be administered (e.g., orally such as by drinking the composition, intravenously) to a subject. In some embodiments, the liquid hydrogen and/or liquid noble gas(es) may dissolve and/or become gaseous. In some cases, the subject may self-administer the composition (e.g., the subject drinks the composition from a container, such as a can). In certain embodiments, the composition may be injected (e.g., via needle) into the subject.

In some cases, the active pharmaceutical agent, liquid hydrogen and/or liquid noble gas(es) may be introduced into a container (e.g., an open container comprising a composition). For example, as illustrated schematically in FIG. 1, article 100 may comprise a liquid (for example, a composition) 110 disposed in container 120. In certain embodiments, the container may be sealed, e.g., to the external atmosphere, e.g., containing the liquid hydrogen and/or liquid noble gases inside. For example, in certain embodiments, the container may be sealed such that the active pharmaceutical agent, liquid and/or gases (e.g., hydrogen gas, and/or xenon gas) within the container are not able to substantially exit the container after sealing. In some embodiments, liquid hydrogen and/or liquid noble gas(es) may be introduced into the container (and/or added to the composition) and the container is sealed such that, upon expansion and change of phase of the liquids into gases (e.g., via heating of the liquids to more ambient temperatures), the hydrogen gas and/or noble gas increases the pressure within the sealed container.

Figure 2A:
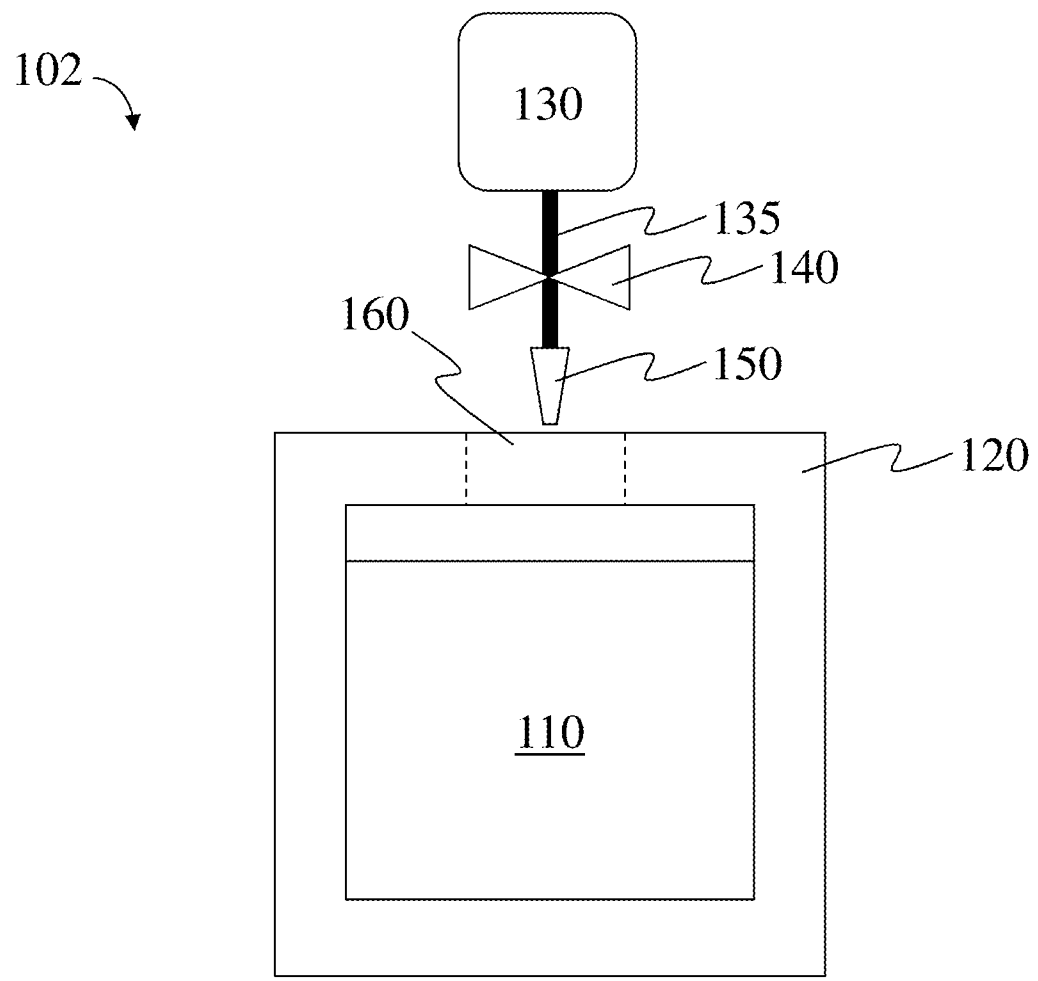
FIG. 2A shows a schematic cross-sectional drawing illustrating a system comprising a source of liquid hydrogen, according to one set of embodiments.

In some embodiments, a system comprising a source of liquid hydrogen and/or liquid noble gas(es) may be used to introduce the liquid hydrogen and/or liquid noble gas(es) into the container (and/or a liquid disposed therein). For example, as illustrated in FIG. 2A, system 102 comprises source 130 (e.g., a storage container) comprising liquid hydrogen and/or liquid noble gas(es). Source 130 may be associated with one or more containers (e.g., container 120) to introduce liquid hydrogen and/or liquid noble gas(es) into the container(s). In some embodiments, valve 140 may be in fluidic communication (e.g., via conduit 135 such as a channel or pipe) with source 130. In certain embodiments, valve 140 is configured and designed for controlling the flow of liquid hydrogen and/or liquid noble gas(es) (e.g., such that the liquid hydrogen and/or liquid noble gas(es) may be introduced into a composition). In some cases, a dispenser 150 may be in fluidic communication with valve 140 and/or source 130. In some embodiments, dispenser 150 is configured and arranged to introduce the liquid hydrogen (e.g., greater than or equal to 0.1 mg of liquid hydrogen) and/or liquid noble gas(es) (e.g., greater than or equal to 0.1 mg of liquid noble gas(es)) into container 120.

Figure 2B:
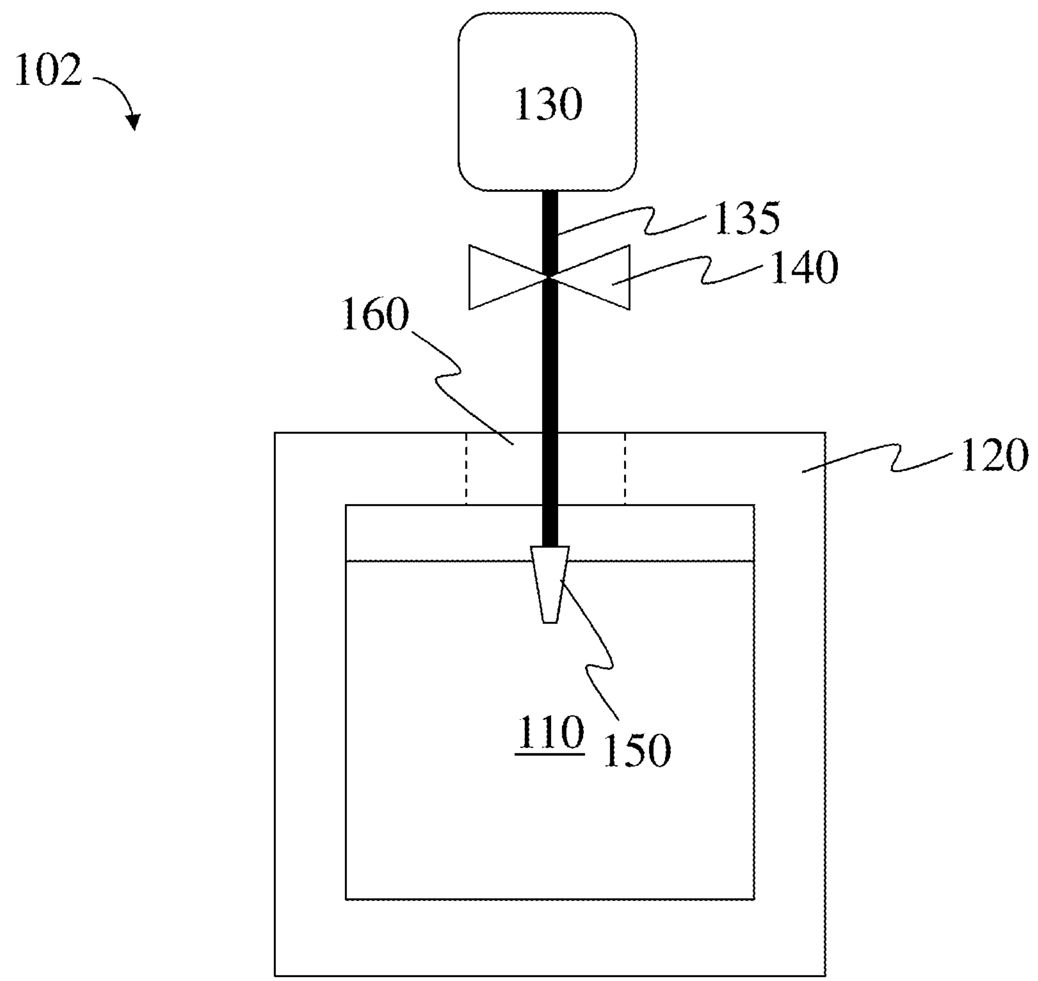
FIG. 2B shows a schematic cross-sectional drawing illustrating a system comprising a source of liquid hydrogen, according to one set of embodiments.

In certain embodiments, dispenser 150 may be positioned proximate an opening (e.g., opening 160) of container 120 such that the liquid hydrogen and/or liquid noble gas(es) may be introduced into container 120 (and/or liquid 110 disposed therein). In some cases, the dispenser may be placed in direct contact with the liquid disposed within the container such that the liquid hydrogen and/or liquid noble gas(es) (e.g., from the source) may be introduced directly into the liquid. For example, as illustrated in FIG. 2B, dispenser 150 may be positioned to be in direct contact with liquid 110 disposed within container 120. In some such embodiments, liquid hydrogen (e.g., greater than or equal to 0.1 mg of liquid hydrogen) and/or liquid noble gas(es) (e.g., greater than or equal to 0.1 mg of liquid noble gas(es)) may be introduced directly into liquid 110.

In some cases, the seal may be removable (e.g., such that the composition may be removed from the container and/or orally administered to a subject, e.g., drunk). For example, in an exemplary embodiment, the container is a can and the can may be unsealed by breaking the seal of the can (e.g., via a pull-tab, push-tab, or stay-tab associated with the seal). In another exemplary embodiment, the container is a bottle or pouch, and the container may be unsealed by removing a cap associated with an opening of the container. Upon unsealing of the container, the composition may be ingested (e.g., drunk) by the subject. In some cases, the container may be used for intravenous infusion, or other administration techniques such as those described herein.

Non-limiting examples of suitable types of containers include cans (e.g., aluminum or tin cans), bottles, jars, pouches, boxes, bags (e.g., IV bags), and capsules (e.g., a liquid gel capsule). Other containers are also possible and those of ordinary skill in the art would be capable of selecting suitable containers based upon the teachings of this specification. The container may also comprise any suitable material. For example, in some embodiments, the container may comprise a material such as metal (e.g., aluminum, tin, iron, etc.), metal alloys (e.g., steel), polymer (e.g., polyethylene, polystyrene, polypropylene, polyether ether ketones, polyethylene terephthalate, polyvinylchloride), glass (e.g., borosilicate glass), resin, and combinations thereof. In certain embodiments, the fluid is present in the container is at or near atmospheric pressure. In some cases, however, the container is able to contain an elevated pressure therein (e.g., a pressure greater than atmospheric pressure).

In addition, in some embodiments, one or more coatings or other materials may be used to facilitate retention of gases within the container, e.g., such materials may be relatively gas-impermeable. A variety of gas-impermeable materials may be readily obtained commercially, and coated onto a surface of the container and/or embedded within the materials forming the container. Non-limiting examples of gas-impermeable materials include polyester, nylon (e.g., MXD6 nylon or nylon 6), ethylene vinyl alcohol (EVA), silicon oxides ($SiO_x$), or the like.

In certain embodiments, the container has a volume of less than about 100 mL, less than 75 mL, less than 50 mL, less than 25 mL, less than 10 mL, less than 5 mL, less than 3 mL, or less than 1 mL. In some cases, the volume of liquid is at least 1 mL, at least 3 mL, at least 5 mL, at least 10 mL, at least 25 mL, at least 50 mL, or at least 75 mL. Combinations of the above-referenced ranges are also possible (e.g., between 75 mL and 10 mL). Other ranges are also possible.

In some embodiments, the container may have a particular volume such as a volume of greater than or equal to 100 mL (e.g., greater than or equal to 250 mL, greater than or equal to 500 mL, greater than or equal to 750 mL, or greater than or equal to 1 L). In certain embodiments, the container has a volume of less than or equal to 2 L (e.g., less than or equal to 1 L, less than or equal to 750 mL, less than or equal to 500 mL, or less than or equal to 250 mL). Combinations of the above-references are also possible (e.g., greater than or equal to 100 mL and less than or equal to 2 L). Other ranges are also possible. In some cases, for instance, the volume of the container may be about 150 mL, about 200 mL, about 222 mL, about 237 mL, about 250 mL, about 330 mL, about 341 mL, about 350 mL, about 355 mL, about 375 mL, about 440 mL, about 473 mL, about 500 mL, about 568 mL, or about 1,000 mL.

The liquid hydrogen may be introduced into the composition in a particular amount. In some embodiments, greater than or equal to 0.1 mg, greater than or equal to 0.2 mg, greater than or equal to 0.3 mg, greater than or equal to 0.4 mg, greater than or equal to 0.5 mg, greater than or equal to 0.6 mg, greater than or equal to 0.7 mg, greater than or equal to 0.8 mg, greater than or equal to 0.9 mg, greater than or equal to 1 mg, greater than or equal to 1.1 mg, greater than or equal to 1.2 mg, greater than or equal to 1.25 mg, greater than or equal to 1.3 mg, greater than or equal to 1.4 mg, greater than or equal to 1.5 mg, greater than or equal to 1.6 mg, greater than or equal to 1.7 mg, greater than or equal to 1.75 mg, greater than or equal to 1.8 mg, greater than or equal to 1.9 mg, greater than or equal to 2 mg, greater than or equal to 2.25 mg, greater than or equal to 2.5 mg, greater than or equal to 2.75 mg, greater than or equal to 3 mg, greater than or equal to 3.25 mg, greater than or equal to 3.5 mg, greater than or equal to 3.75 mg, greater than or equal to 4 mg, greater than or equal to 4.25 mg, greater than or equal to 4.5 mg, or greater than or equal to 4.75 mg of liquid hydrogen is added per liter of composition. Without wishing to be bound by theory, 1 mg of liquid hydrogen generally corresponds to a volume of approximately 14 microliters based upon a density of 70.8 mg/mL of liquid hydrogen.

In certain embodiments, the liquid hydrogen is added to the composition in an amount of less than or equal to 5 mg, less than or equal to 4.75 mg, less than or equal to 4.5 mg, less than or equal to 4.25 mg, less than or equal to 4 mg, less than or equal to 3.75 mg, less than or equal to 3.5 mg, less than or equal to 3.25 mg, less than or equal to 3 mg, less than or equal to 2.75 mg, less than or equal to 2.5 mg, less than or equal to 2.25 mg, less than or equal to 2 mg, less than or equal to 1.9 mg, less than or equal to 1.8 mg, less than or equal to 1.75 mg, less than or equal to 1.7 mg, less than or equal to 1.6 mg, less than or equal to 1.5 mg, less than or equal to 1.4 mg, less than or equal to 1.3 mg, less than or equal to 1.25 mg, less than or equal to 1.2 mg, less than or equal to 1.1 mg, less than or equal to 1 mg, less than or equal to 0.9 mg, less than or equal to 0.8 mg, less than or equal to 0.7 mg, less than or equal to 0.6 mg, less than or equal to 0.5 mg, less than or equal to 0.4 mg, less than or equal to 0.3 mg, or less than or equal to 0.2 mg of liquid hydrogen per liter of composition. Combinations of the above-referenced ranges are also possible (e.g., greater than or equal to 0.1 mg and less than or equal to 5 mg, greater than or equal to 1.5 mg and less than or equal to 2 mg per liter of composition).

In some cases, the liquid hydrogen may be introduced into a composition such that at least a portion of the liquid hydrogen (e.g., substantially all of the liquid hydrogen) changes phase into a gas at a particular concentration (e.g., upon sealing of a container comprising the composition and expanded hydrogen gas) relative to the composition. For example, this may occur as the liquid hydrogen is heated upon exposure to the composition, and/or upon sealing of the container containing the liquid hydrogen and composition. In some embodiments, the concentration of hydrogen gas present in the container (e.g., upon sealing of the container) and dissolved in the composition is greater than or equal to 0.1 ppm, greater than or equal to 0.2 ppm, greater than or equal to 0.3 ppm, greater than or equal to 0.4 ppm, greater than or equal to 0.5 ppm, greater than or equal to 0.6 ppm, greater than or equal to 0.7 ppm, greater than or equal to 0.8 ppm, greater than or equal to 0.9 ppm, greater than or equal to 1 ppm, greater than or equal to 1.1 ppm, greater than or equal to 1.2 ppm, greater than or equal to 1.25 ppm, greater than or equal to 1.3 ppm, greater than or equal to 1.4 ppm, greater than or equal to 1.5 ppm, greater than or equal to 1.6 ppm, greater than or equal to 1.7 ppm, greater than or equal to 1.75 ppm, greater than or equal to 1.8 ppm, greater than or equal to 1.9 ppm, greater than or equal to 2 ppm, greater than or equal to 2.25 ppm, greater than or equal to 2.5 ppm, greater than or equal to 2.75 ppm, greater than or equal to 3 ppm, greater than or equal to 3.25 ppm, greater than or equal to 3.5 ppm, greater than or equal to 3.75 ppm, greater than or equal to 4 ppm, greater than or equal to 4.25 ppm, greater than or equal to 4.5 ppm, or greater than or equal to 4.75 ppm. In certain embodiments, the hydrogen gas is present in the composition in an amount of less than or equal to 5 ppm, less than or equal to 4.75 ppm, less than or equal to 4.5 ppm, less than or equal to 4.25 ppm, less than or equal to 4 ppm, less than or equal to 3.75 ppm, less than or equal to 3.5 ppm, less than or equal to 3.25 ppm, less than or equal to 3 ppm, less than or equal to 2.75 ppm, less than or equal to 2.5 ppm, less than or equal to 2.25 ppm, less than or equal to 2 ppm, less than or equal to 1.9 ppm, less than or equal to 1.8 ppm, less than or equal to 1.75 ppm, less than or equal to 1.7 ppm, less than or equal to 1.6 ppm, less than or equal to 1.5 ppm, less than or equal to 1.4 ppm, less than or equal to 1.3 ppm, less than or equal to 1.25 ppm, less than or equal to 1.2 ppm, less than or equal to 1.1 ppm, less than or equal to 1 ppm, less than or equal to 0.9 ppm, less than or equal to 0.8 ppm, less than or equal to 0.7 ppm, less than or equal to 0.6 ppm, less than or equal to 0.5 ppm, less than or equal to 0.4 ppm, less than or equal to 0.3 ppm, or less than or equal to 0.2 ppm. Combinations of the above-referenced ranges are also possible (e.g., greater than or equal to 0.1 ppm and less than or equal to 5 ppm, greater than or equal to 1.5 ppm and less than or equal to 2 ppm). Other ranges are also possible. In addition, in some embodiments, no liquid hydrogen may be present.

Liquid hydrogen has a boiling point of 20 K (−253° C.) at 1 bar. Higher pressures may cause the boiling point of hydrogen to increase. Thus, liquid hydrogen at various pressures, may have a boiling point of less than 25 K, less than 30 K, or less than 33 K (e.g., at 1.29 MPa, the critical point of hydrogen). Thus, the liquid hydrogen in certain embodiments may be kept at a temperature less than its boiling point (e.g., at a suitable pressure). In addition, in some cases, the liquid hydrogen may be present in supercritical state, e.g., during storage and/or upon introduction to a container or a composition. It should thus be understood that "liquid hydrogen," as used herein, includes both subcritical hydrogen and supercritical hydrogen. In some cases, however, the liquid hydrogen is only in a supercritical state. In addition, in some cases, the liquid hydrogen is only in a subcritical state.

Non-limiting examples of suitable liquid noble gases that may be introduced to the composition include helium, neon, argon, krypton, and xenon, as well as combinations thereof. It should be understood that these elements are generally referred to in the art as "noble gases," irrespective of the state of the matter that they happen to be in, i.e., a "noble gas" may be a solid, liquid, or gas. (At room temperature, the noble gases are gases, but that should not be read to imply that the noble gases cannot also achieve other states of matter, such as liquids.)

In a particular set of embodiments, the liquid noble gas is liquid xenon. In some cases, two or more liquid noble gases may be present, e.g., each independently at the concentrations below. The liquid noble gas may be introduced to the composition such that the liquid noble gas changes phase into a gas and is substantially dissolved and/or suspended in the composition. For example, the mole fraction solubility of xenon in water at 25° C. and 1 atm is generally $7.890\times10^{-5}$. In some embodiments, the amount of noble gas dissolved in the composition is greater than the amount of noble gas that would be dissolved in the composition at the mole fraction solubility of the noble gas in water determined at 25° C. and 1 atm. For example, the composition may be under a pressure greater than 1 atm and/or a temperature greater than 25° C., e.g., as discussed herein, which may facilitate greater amounts.

In some cases, the liquid noble gas does not substantially change phase into a gas (e.g., while stored in a container containing the composition).

The liquid noble gas may be introduced into the composition in a particular amount. In some embodiments, greater than or equal to 0.1 mg, greater than or equal to 0.2 mg, greater than or equal to 0.3 mg, greater than or equal to 0.4 mg, greater than or equal to 0.5 mg, greater than or equal to 0.6 mg, greater than or equal to 0.7 mg, greater than or equal to 0.8 mg, greater than or equal to 0.9 mg, greater than or equal to 1 mg, greater than or equal to 1.1 mg, greater than or equal to 1.2 mg, greater than or equal to 1.25 mg, greater than or equal to 1.3 mg, greater than or equal to 1.4 mg, greater than or equal to 1.5 mg, greater than or equal to 1.6 mg, greater than or equal to 1.7 mg, greater than or equal to 1.75 mg, greater than or equal to 1.8 mg, greater than or equal to 1.9 mg, greater than or equal to 2 mg, greater than or equal to 2.25 mg, greater than or equal to 2.5 mg, greater than or equal to 2.75 mg, greater than or equal to 3 mg, greater than or equal to 3.25 mg, greater than or equal to 3.5 mg, greater than or equal to 3.75 mg, greater than or equal to 4 mg, greater than or equal to 4.25 mg, greater than or equal to 4.5 mg, greater than or equal to 4.75 mg, greater than or equal to 5 mg, greater than or equal to 5.5 mg, greater than or equal to 6 mg, greater than or equal to 6.5 mg, greater than or equal to 7 mg, greater than or equal to 7.5 mg, greater than or equal to 8 mg, greater than or equal to 8.5 mg, greater than or equal to 9 mg, greater than or equal to 9.5 mg, greater than or equal to 10 mg, greater than or equal to 11 mg, greater than or equal to 12 mg, greater than or equal to 13 mg, greater than or equal to 14 mg, greater than or equal to 15 mg, greater than or equal to 16 mg, greater than or equal to 17 mg, greater than or equal to 18 mg, or greater than or equal to 19 mg of liquid noble gas (e.g., liquid xenon) is added per liter of composition.

Without wishing to be bound by theory, 1 mg of liquid xenon generally corresponds to a volume of approximately 0.32 microliters based upon a density of 3.1 mg/microliters of liquid xenon.

In certain embodiments, the liquid noble gas is added to the composition in an amount of less than or equal to 20 mg, less than or equal to 19 mg, less than or equal to 18 mg, less than or equal to 17 mg, less than or equal to 16 mg, less than or equal to 15 mg, less than or equal to 14 mg, less than or equal to 13 mg, less than or equal to 12 mg, less than or equal to 11 mg, less than or equal to 10 mg, less than or equal to 9.5 mg, less than or equal to 9 mg, less than or equal to 8.5 mg, less than or equal to 8 mg, less than or equal to 7.5 mg, less than or equal to 7 mg, less than or equal to 6.5 mg, less than or equal to 6 mg, less than or equal to 5.5 mg, less than or equal to 5 mg, less than or equal to 4.75 mg, less than or equal to 4.5 mg, less than or equal to 4.25 mg, less than or equal to 4 mg, less than or equal to 3.75 mg, less than or equal to 3.5 mg, less than or equal to 3.25 mg, less than or equal to 3 mg, less than or equal to 2.75 mg, less than or equal to 2.5 mg, less than or equal to 2.25 mg, less than or equal to 2 mg, less than or equal to 1.9 mg, less than or equal to 1.8 mg, less than or equal to 1.75 mg, less than or equal to 1.7 mg, less than or equal to 1.6 mg, less than or equal to 1.5 mg, less than or equal to 1.4 mg, less than or equal to 1.3 mg, less than or equal to 1.25 mg, less than or equal to 1.2 mg, less than or equal to 1.1 mg, less than or equal to 1 mg, less than or equal to 0.9 mg, less than or equal to 0.8 mg, less than or equal to 0.7 mg, less than or equal to 0.6 mg, less than or equal to 0.5 mg, less than or equal to 0.4 mg, less than or equal to 0.3 mg, or less than or equal to 0.2 mg of liquid noble gas per liter of composition. Combinations of the above-referenced ranges are also possible (e.g., greater than or equal to 1 mg and less than or equal to 20 mg, greater than or equal to 10 mg and less than or equal to 15 mg, greater than or equal to 0.1 mg and less than or equal to 5 mg, greater than or equal to 1.5 mg and less than or equal to 2 mg per liter of composition).

In some cases, one or more liquid noble gases may be introduced into a composition such that at least a portion of the liquid noble gas (e.g., substantially all of the liquid noble gas) changes phase into a gas at a particular concentration (e.g., upon sealing of a container comprising the composition and expanded noble gas) relative to the composition. For example, this may occur as the one or more liquid noble gases are heated upon exposure to the composition, and/or upon sealing of the container containing the liquid hydrogen and composition. In some embodiments, the concentration of noble gas present in the container (e.g., upon sealing of the container) and dissolved in the composition is greater than or equal to 1 ppm, greater than or equal to 1.25 ppm, greater than or equal to 1.5 ppm, greater than or equal to 1.75 ppm, greater than or equal to 2 ppm, greater than or equal to 2.25 ppm, greater than or equal to 2.5 ppm, greater than or equal to 2.75 ppm, greater than or equal to 3 ppm, greater than or equal to 3.25 ppm, greater than or equal to 3.5 ppm, greater than or equal to 3.75 ppm, greater than or equal to 4 ppm, greater than or equal to 4.25 ppm, greater than or equal to 4.5 ppm, greater than or equal to 4.75 ppm, greater than or equal to 5 ppm, greater than or equal to 5.5 ppm, greater than or equal to 6 ppm, greater than or equal to 6.5 ppm, greater than or equal to 7 ppm, greater than or equal to 7.5 ppm, greater than or equal to 8 ppm, greater than or equal to 8.5 ppm, greater than or equal to 9 ppm, greater than or equal to 9.5 ppm, greater than or equal to 10 ppm, greater than or equal to 11 ppm, greater than or equal to 12 ppm, greater than or equal to 13 ppm, greater than or equal to 14 ppm, greater than or equal to 15 ppm, greater than or equal to 16 ppm, greater than or equal to 17 ppm, greater than or equal to 18 ppm, or greater than or equal to 19 ppm. In certain embodiments, the noble gas is present in the composition in an amount of less than or equal to 20 ppm, less than or equal to 19 ppm, less than or equal to 18 ppm, less than or equal to 17 ppm, less than or equal to 16 ppm, less than or equal to 15 ppm, less than or equal to 14 ppm, less than or equal to 13 ppm, less than or equal to 12 ppm, less than or equal to 11 ppm, less than or equal to 10 ppm, less than or equal to 9.5 ppm, less than or equal to 9 ppm, less than or equal to 8.5 ppm, less than or equal to 8 ppm, less than or equal to 7.5 ppm, less than or equal to 7 ppm, less than or equal to 6.5 ppm, less than or equal to 5 ppm, less than or equal to 4.75 ppm, less than or equal to 4.5 ppm, less than or equal to 4.25 ppm, less than or equal to 4 ppm, less than or equal to 3.75 ppm, less than or equal to 3.5 ppm, less than or equal to 3.25 ppm, less than or equal to 3 ppm, less than or equal to 2.75 ppm, less than or equal to 2.5 ppm, less than or equal to 2.25 ppm, less than or equal to 2 ppm, less than or equal to 1.75 ppm, less than or equal to 1.5 ppm, or less than or equal to 1.25 ppm. Combinations of the above-referenced ranges are also possible (e.g., greater than or equal to 1 ppm and less than or equal to 20 ppm, greater than or equal to 10 ppm and less than or equal to 15 ppm). Other ranges are also possible. The noble gas may include xenon, and/or other gases as discussed herein. In other embodiments, however, no liquid noble gases may be used.

Liquid xenon has a boiling point of 165 K (−108° C.) at 1 bar. Similarly, the boiling points of helium, neon, argon, krypton are, respectively 4 K, 25 K, 87 K, 116 K. Higher pressures may cause the boiling point of the noble gas to increase. Thus, for example, liquid xenon at various pressures may have a boiling point of less than 170 K, less than 180 K, less than 190 K, less than 200 K, less than 210 K, less than 210 K, less than 220 K, less than 230 K, less than 240 K, less than 250 K, less than 260 K, less than 270 K, less than 280 K, or less than 290 K (e.g., at 5.8 MPa, the critical point of xenon). A liquid noble gas, in certain embodiments, may be kept at a temperature less than its boiling point (e.g., at a suitable pressure), e.g., at temperatures less than the above temperatures.

In addition, in some cases, the liquid noble gas may be present in supercritical state, e.g., during storage and/or upon introduction to a container or a composition. It should thus be understood that a "liquid noble gas," as used herein, includes both noble gases in the subcritical and supercritical states. In some cases, e.g., if more than one noble gas is present, they may each be independently present in a subcritical or supercritical state, e.g., depending on the temperature and/or pressure. In some cases, however, all of the noble gas is present only in a supercritical state. In addition, in some cases, all of the noble gas is present only in a subcritical state.

In an exemplary embodiment, the composition is configured for intravenous delivery of the composition contained therein to a subject and comprises saline (e.g., NaCl dissolved in water as excipient), an active pharmaceutical agent, and liquid hydrogen and/or liquid noble gas(es). In some cases, the composition may be normal saline (i.e. 0.9 wt %/vol % NaCl per total volume of the water present in the composition) and comprises an active pharmaceutical agent, hydrogen gas and/or noble gas(es). In some embodiments, NaCl is present in the composition in an amount of greater than or equal to 0.1 wt %, greater than or equal to 0.2 wt %, greater than or equal to 0.3 wt %, greater than or equal to 0.5 wt %, greater than or equal to 0.7 wt %, greater than or equal to 0.9 wt %, greater than or equal to 1 wt %, greater than or equal to 1.2 wt %, greater than or equal to 1.5 wt %, greater than or equal to 1.7 wt %, or greater than or equal to 2 wt % per total volume of the water present in the composition). In certain embodiments, NaCl is present in the composition in an amount of less than or equal to 2.5 wt %, less than or equal to 2 wt %, less than or equal to 1.7 wt %, less than or equal to 1.5 wt %, less than or equal to 1.2 wt %, less than or equal to 1 wt %, less than or equal to 0.9 wt %, less than or equal to 0.7 wt %, less than or equal to 0.5 wt %, less than or equal to 0.3 wt %, or less than or equal to 0.2 wt %. Combinations of the above-referenced ranges are also possible (e.g., greater than or equal to 0.1 wt % and less than or equal to 2.5 wt %, greater than or equal to 0.7 wt % and less than or equal to 1 wt %). Other ranges are also possible.

In some cases, the system comprises a valve and/or other components (e.g., pipes, pressure gauges) configured and designed for the introduction of liquid hydrogen and/or liquid noble gas(es) into a composition, e.g., within a container or other article. Such valves and/or other components, in some cases, may be designed to flow and/or dispense particularly cold liquids (e.g., liquid hydrogen) such that the liquid does not substantially change phase (e.g., until exiting, for example, into a container comprising a composition). In some embodiments, the liquid hydrogen and/or liquid noble gas(es) is flowed through the system comprising a valve (e.g., a valve in fluidic communication with a source for the liquid hydrogen and/or liquid noble gas(es)) configured and designed for the introduction of cryogenic liquids such as liquid hydrogen and/or liquid noble gas(es).

In one set of embodiments, the system may include a system for removing gaseous hydrogen. For example, in certain embodiments, the system comprises a source of inert gas (for example, air, nitrogen, carbon dioxide, etc.). The source of inert gas may be, for example, a gas cylinder, a pressure tank, an HVAC system, or the like. In some cases, the system may be configured such that the inert gas is introduced proximate the valve and/or other components, e.g., to displace or dilute gaseous hydrogen from around the system. In some cases, the inert gas may be blown (e.g., by a fan) or otherwise provided proximate the valve and/or other components such that e.g., the presence of gaseous hydrogen, if present, outside of the valve and/or other components may be mitigated. In some cases, the inert gas may not be directed at a specific location (e.g., via a pipe, duct, tube, etc.), but simply allowed to vent around at least a portion of the system to displace any gaseous hydrogen that may be present. In other cases, however, the gas may be directed to a specific location within the system, for example, at a valve and/or other component, using one or more pipes, ducts, tubes, etc.

As another example, a fan, a ventilation system, a blower, or the like may be used to remove the gaseous hydrogen. Without wishing to be bound by theory, unlike inert gases such as nitrogen, hydrogen may present a risk of ignition and/or explosion if unmitigated and, as such, the safety considerations for dispensing liquid hydrogen (e.g., which may boil and/or evaporate under ambient conditions producing gaseous hydrogen) are substantially different than those for dispensing liquid nitrogen. Advantageously, the removal of gaseous hydrogen, for example, with the introduction of inert gas and/or air, may reduce or eliminate the risk of ignition and/or explosion of relatively explosive gases such as gaseous hydrogen that may, in some cases, inadvertently leak from the system, e.g., from the valve and/or other components.

In one set of embodiments, the system comprises one, two, or more storage containers for containing one or more liquids (e.g., at cryogenic temperatures, such as the temperatures disclosed herein. In some cases, for example, the temperature within a storage container may be less than 300 K, less than 290 K, less than 280 K, less than 270 K, less than 260 K, less than 250 K, less than 240 K, less than 230 K, less than 220 K, less than 210 K, less than 200 K, less than 190 K, less than 180 K, less than 170 K, less than 160 K, less than 150 K, less than 140 K, less than 130 K, less than 120 K, less than 110 K, less than 100 K, less than 90 K, less than 80 K, less than 77 K, less than 75 K, less than 70 K, less than 65 K, less than 60 K, less than 55 K, less than 50 K, less than 45 K, less than 40 K, less than 35 K, less than 30 K, less than 25 K, less than 20 K, or less than 10 K.

The storage container may be unpressurized (e.g., at atmospheric pressure, 1 atm), or may have a pressure than is greater or less than atmospheric pressure. In some embodiments, the pressure may be less than 10 MPa, less than 9 MPa, less than 8 MPa, less than 7 MPa, less than 6 MPa, less than 5 MPa, less than 4 MPa, less than 3 MPa, less than 2 MPa, less than 1 MPa, less than 900 kPa, less than 800 kPa, less than 700 kPa, less than 600 kPa, less than 500 kPa, less than 400 kPa, less than 300 kPa, or less than 200 kPa. In addition, in some cases, the pressure may also be greater than atmospheric pressure, or greater than 100 kPa, greater than 200 kPa, greater than 300 kPa, greater than 400 kPa, greater than 500 kPa, greater than 600 kPa, greater than 700 kPa, greater than 800 kPa, greater than 900 kPa, greater than 1 MPa, greater than 2 MPa, greater than 3 MPa, greater than 4 MPa, greater than 5 MPa, greater than 6 MPa, greater than 7 MPa, greater than 8 MPa, greater than 9 MPa, greater than 10 MPa, etc. Combinations of any of these are possible, e.g., a container may have a pressure between 300 kPa and 1 MPa. Other pressures are also possible. In addition, if more than one storage container is present, the temperature and/or pressure of the storage containers may be the same or different.

The storage containers may, in some cases, be pressurized and/or thermally insulated containers. In some embodiments, a storage container may formed out of a metal, such as stainless steel. The storage container may also be vacuum-insulted in some cases. In some cases, the storage container is a Dewar flask. Dewar and other vacuum-insulated containers may be obtained commercially. In some cases, an inert gas and/or air may be introduced proximate the storage containers (e.g., to reduce or eliminate the risk of ignition and/or explosion by one or more flammable gases).

One or more storage containers (e.g., sources of liquid hydrogen and/or liquid noble gas(es)) may be in fluidic communication with a valve, optionally via one or more conduits (e.g., pipes). For example, as illustrated in FIG. 2A, valve 140 is in fluidic communication with source 130 (e.g., comprising liquid hydrogen and/or liquid noble gas(es) stored therein). In some embodiments, the valve may comprise one or more materials suitable for controlling the flow of relatively cold liquids (e.g., a cryogenic liquid). In an exemplary embodiment, the valve comprises austenitic stainless steel, steel alloys, carbon steel, polytetrafluoroethylene, or combinations thereof. The valve may be, for example, a globe valve, a gate valve, a check valve, a butterfly valve, a cryogenic ball valve, or combinations thereof. The valve may disperse cryogenic liquids into a container, and in some cases, in a relatively controlled dose, e.g., such that the amount of liquid that flows into each container is substantially the same. For example, 80%, 85%, 90%, or 95% of the containers may contain between 80% and 120%, between 85% and 115%, between 90% and 110%, or between 95% and 105% of the average amount of liquid deposited into the containers.

In some cases, the valve may be used to regulate the flow of liquid hydrogen and/or liquid noble gas(es) during and between introducing the liquids into one or more containers. For example, the valve may be open such that the liquid hydrogen and/or liquid noble gas(es) are introduced into each container and, in some cases, the valve may be closed such that liquid hydrogen and/or liquid noble gas(es) is not dispensed outside of each container (e.g., to prevent loss of liquid). One or more control systems (e.g., computerized control systems) may be associated with the valve (e.g., to control the opening and closing of the valve). In some embodiments, the control system may be associated with the valve and configured such that valve disperses cryogenic liquids into a container, and in some cases, in a relatively controlled dose, e.g., such that the amount of liquid that flows into each container is substantially the same. In some cases, the position or degree of the opening of the valve may also be controlled, e.g., the valve may be fully open, 50% open, 20% open, or fully closed, etc.

In certain embodiments, the valve comprises and/or is associated with one or more pressure regulators (e.g., to control the pressure and/or flow rate of the liquid hydrogen and/or noble gas(es) through the valve). In some embodiments, the pressure regulator is in fluidic communication with the valve. In some such embodiments, the pressure regulator may be configured and designed for regulating the flow rate and/or pressure of cryogenic liquids. Such pressure regulators may comprise austenitic stainless steel, steel alloys, carbon steel, polytetrafluoroethylene, or combinations thereof. In certain embodiments, the pressure regulator is configured such that the cryogenic liquid is introduced into one or more containers in a relative controlled dose (e.g., such that the amount of liquid that flows into each container is substantially the same) and/or at a relatively controlled rate (e.g., at a rate of greater than or equal to 100 containers per minute).

In some cases, the valve further comprises a gas purge which allows gases (e.g., hydrogen and/or noble gases) to escape the system. As insulation is generally not perfect, some amount of liquid may be heated to form gas, e.g., within the storage containers and/or prior to reaching the valve, e.g., during flow through one or more conduits. Such gases may be purged, e.g., via a gas purge, such that the gases are not delivered to the containers, but instead are purged (e.g., to the atmosphere).

In one set of embodiments, the valve may comprise a heater, e.g., to remove potential blockage or "freeze-ups" of the valve. For example, water vapor (e.g., from the ambient environment) may condense on the valves, which could lead to ice formation, blockage, or disruption of the flow of liquid through the valve. The heater may comprise any suitable means for heating the valve and/or one or more conduits in fluidic communication with the valve. Non-limiting examples of such heaters include, for example, heat tape (e.g., silicone-based heat tape), electrical heaters, heat exchangers, heating via a suitable heating fluid (which may be a liquid or a gas, such as air). Other heaters may also be used in other embodiments. In some cases, an insulative material may be associated with the valve(s) and/or conduit(s) to prevent and/or reduce potential blockage or "freeze-ups."

In addition, in some cases, the liquids flowing through the valve may also solidify within the valve. Accordingly, in some embodiments, a heater (and/or insulative material) may be used periodically to remove any freeze-ups, blockage, or disruption of the flow of liquid through the valve. The heater may be, for example, an electrical heater, In some embodiments, the system is in fluidic communication with a dispenser associated with one or more containers (e.g., such that the liquid hydrogen and/or liquid noble gas(es) may be introduced into the one or more containers). In certain embodiments, the system may introduce liquid hydrogen and/or liquid noble gas(es) into one or more containers relatively rapidly. For example, in some embodiments, the system may be configured to introduce liquid hydrogen and/or liquid noble gas(es) (e.g., greater than or equal to 0.1 mg of liquid hydrogen and/or liquid noble gas(es)) into one or more containers at a rate of greater than or equal to 100 containers per minute, greater than or equal to 150 containers per minute, greater than or equal to 200 containers per minute, greater than or equal to 250 containers per minute, greater than or equal to 300 containers per minute, greater than or equal to 350 containers per minute, greater than or equal to 400 containers per minute, greater than or equal to 450 containers per minute, greater than or equal to 500 containers per minute, greater than or equal to 600 containers per minute, greater than or equal to 700 containers per minute, greater than or equal to 800 containers per minute, greater than or equal to 900 containers per minute, or greater than or equal to 1000 containers per minute. In certain embodiments, the system may be configured to introduce liquid hydrogen and/or liquid noble gas(es) into one or more containers at a rate of less than or equal to 1000 containers per minute, less than or equal to 900 containers per minute, less than or equal to 800 containers per minute, less than or equal to 700 containers per minute, less than or equal to 600 containers per minute, less than or equal to 500 containers per minute, less than or equal to 450 containers per minute, less than or equal to 400 containers per minute, less than or equal to 350 containers per minute, less than or equal to 300 containers per minute, less than or equal to 250 containers per minute, less than or equal to 200 containers per minute, or less than or equal to 150 containers per minute. Combinations of the above-referenced ranges are also possible (e.g., greater than or equal to 100 containers per minute and less than or equal to 1000 containers per minute). Other ranges are also possible.

In certain embodiments, after dispensing of the liquid hydrogen and/or liquid noble gas(es) into one or more containers, the liquid comprising liquid hydrogen and/or liquid noble gas(es) may be administered (e.g., orally) to a subject (including self-administered).

In some embodiments, the compositions and/or containers described herein are configured to have a relatively long shelf life with respect to the gases contained therein. In certain embodiments, the hydrogen gas and noble gas (e.g., xenon gas) does not substantially leak from the sealed container for at least 7 days, or longer (e.g., 14 days, 28 days, 56 days, etc.). For example, in some embodiments, greater than or equal to 50 vol %, greater than or equal to 75 vol %, greater than or equal to 80 vol %, greater than or equal to 85 vol %, greater than or equal to 90 vol %, greater than or equal to 92 vol %, greater than or equal to 95 vol %, greater than or equal to 98 vol %, greater than or equal to 99 vol %, greater than or equal to 99.5 vol %, or greater than or equal to 99.9 vol % of the hydrogen gas and/or xenon gas (and/or other noble gases) is present in the sealed container and/or in the headspace 7 days after sealing of the container (including the liquid comprising the hydrogen gas and the noble gas). In certain embodiments, less than or equal to 99.99 vol %, less than or equal to 99.9 vol %, less than or equal to 99.5 vol %, less than or equal to 99 vol %, less than or equal to 98 vol %, less than or equal to 95 vol %, less than or equal to 92 vol %, less than or equal to 90 vol %, less than or equal to 85 vol %, less than or equal to 80 vol %, or less than or equal to 75 vol % of the hydrogen gas and/or xenon gas (and/or other noble gases) is present in the sealed container and/or in the headspace 7 days after sealing of the container (including within the composition comprising the hydrogen gas and the noble gas). Combinations of the above-referenced ranges are also possible (e.g., greater than or equal to 50 vol % and less than or equal to 99.99 vol %). Other ranges are also possible.

In certain embodiments, the articles, compositions, and compositions described herein are substantially non-toxic. The term "non-toxic" refers to a substance that does not comprise a toxic compound. The term "toxic" refers to a substance showing detrimental, deleterious, harmful, or otherwise negative effects on a subject, tissue, or cell when or after administering the substance to the subject or contacting the tissue or cell with the substance, compared to the subject, tissue, or cell prior to administering the substance to the subject or contacting the tissue or cell with the substance. In certain embodiments, the effect is death or destruction of the subject, tissue, or cell. In certain embodiments, the effect is a detrimental effect on the metabolism of the subject, tissue, or cell. In certain embodiments, a toxic substance is a substance that has a median lethal dose (LD50) of not more than 500 milligrams per kilogram of body weight when administered orally to an albino rat weighing between 200 and 300 grams, inclusive. In certain embodiments, a toxic substance is a substance that has an LD50 of not more than 1,000 milligrams per kilogram of body weight when administered by continuous contact for 24 hours (or less if death occurs within 24 hours) with the bare skin of an albino rabbit weighing between two and three kilograms, inclusive. In certain embodiments, a toxic substance is a substance that has an LC50 in air of not more than 2,000 parts per million by volume of gas or vapor, or not more than 20 milligrams per liter of mist, fume, or dust, when administered by continuous inhalation for one hour (or less if death occurs within one hour) to an albino rat weighing between 200 and 300 grams, inclusive.

A "subject" refers to any animal such as a mammal (e.g., a human). Non-limiting examples of subjects include a human, a non-human primate, a cow, a horse, a pig, a sheep, a goat, a dog, a cat or a rodent such as a mouse, a rat, a hamster, a bird, a fish, or a guinea pig. Generally, the invention is directed toward use with humans. In some embodiments, a subject may demonstrate health benefits, e.g., upon administration of the liquid.

As used herein, a "fluid" is given its ordinary meaning, i.e., a liquid or a gas. A fluid cannot maintain a defined shape and will flow during an observable time frame to fill the container in which it is put. Thus, the fluid may have any suitable viscosity that permits flow. If two or more fluids are present, each fluid may be independently selected among essentially any fluids (liquids, gases, and the like) by those of ordinary skill in the art.

A co-owned U.S. patent application filed on Aug. 8, 2017, entitled "Methods and Systems for Preparing Compositions," by Nicholas Perricone is incorporated herein by reference in its entirety for all purposes.

EXAMPLES

The following examples illustrate embodiments of certain aspects of the invention. It should be understood that the methods and/or materials described herein may be modified and/or scaled, as known to those of ordinary skill in the art.

Prophetic Example 1

A composition comprising an active pharmaceutical agent (e.g., THC) is provided. A system comprising a valve configured and designed for the flow of liquid hydrogen is placed into fluidic communication with the composition. Liquid hydrogen is flowed through the system such that greater than or equal to 0.1 mg and less than or equal to 5 mg of liquid hydrogen is introduced to one liter of the composition.

Prophetic Example 2

A composition such as described herein is provided to a subject, such as a human subject. The composition comprises a liquid such as water (or another suitable drink), dissolved hydrogen, and an active pharmaceutical agent (e.g., THC). After ingestion (e.g., being drunk), the effects of the THC are felt by the subject surprisingly rapidly, e.g., less than 5 minutes, as compared to other methods which typically take tens of minutes.

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified unless clearly indicated to the contrary. Thus, as a non-limiting example, a reference to "A and/or B," when used in conjunction with open-ended language such as "comprising" can refer, in one embodiment, to A without B (optionally including elements other than B); in another embodiment, to B without A (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed:

1. A container containing:

an aqueous solution comprising one or more cannabinoids selected from the group consisting of tetrahydrocannabinol and cannabidiol; and greater than or equal to 0.1 mg and less than or equal to 5 mg liquid hydrogen at a temperature of less than 33 Kelvin (K), wherein the container has a volume of less than or equal to 500 mL.

2. A container as in claim 1, wherein the aqueous solution comprises an excipient.

3. A container as in claim 1, wherein the container further contains a liquid noble gas.

4. A container as in claim 1, wherein the one or more cannabinoids comprises tetrahydrocannabinol.

5. A container as in claim 1, wherein the one or more cannabinoids comprises cannabidiol.

6. The container of claim 1, wherein the container has a volume of greater than or equal to 250 mL and less than or equal to 500 mL.

7. The container of claim 1, wherein the container is sealed.

* * * * *